(12) United States Patent
Wong

(10) Patent No.: US 8,329,141 B2
(45) Date of Patent: Dec. 11, 2012

(54) LOCOREGIONAL INTERNAL RADIONUCLIDE ABLATION OF ABNORMAL TISSUES

(75) Inventor: Franklin C. Wong, Bellaire, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1147 days.

(21) Appl. No.: 11/714,295

(22) Filed: Mar. 2, 2007

(65) Prior Publication Data

US 2007/0217998 A1    Sep. 20, 2007

Related U.S. Application Data

(63) Continuation of application No. PCT/US2005/031396, filed on Sep. 2, 2005.

(60) Provisional application No. 60/607,052, filed on Sep. 3, 2004.

(51) Int. Cl.
*A61M 36/14* (2006.01)
*A61K 51/00* (2006.01)

(52) U.S. Cl. ........... 424/1.65; 424/1.11; 424/1.81; 424/1.85; 424/1.89; 424/1.73; 424/9.1

(58) Field of Classification Search .......... 424/1.11, 424/1.65, 1.81, 1.85, 1.89, 9.1, 9.2, 9.3, 9.4, 424/9.5, 9.6, 9.7, 9.8, 1.73
See application file for complete search history.

(56) References Cited

U.S. PATENT DOCUMENTS

| | | | |
|---|---|---|---|
| 4,830,848 A | 5/1989 | Neirinckx et al. | |
| 4,897,254 A | 1/1990 | Simon et al. | |
| 4,898,724 A | 2/1990 | Simon et al. | |
| 5,061,475 A | 10/1991 | Lieberman et al. | |
| 5,066,478 A | 11/1991 | Simon et al. | |
| 5,300,279 A | 4/1994 | Simon et al. | |
| 5,308,606 A | 5/1994 | Wilson et al. | |
| 5,342,604 A | 8/1994 | Wilson et al. | |
| 5,362,473 A | 11/1994 | Panek | |
| 5,762,903 A | 6/1998 | Park et al. | |
| 6,022,521 A * | 2/2000 | Wahl et al. | 424/1.49 |
| 6,238,644 B1 | 5/2001 | Rillema | |
| 6,241,962 B1 | 6/2001 | Nicolini et al. | |
| 6,352,682 B2 | 3/2002 | Leavitt et al. | |
| 6,685,913 B1 | 2/2004 | Thakur | |
| 6,770,020 B2 | 8/2004 | De Stasio et al. | |
| 7,008,633 B2 * | 3/2006 | Yang et al. | 424/422 |
| 7,045,116 B2 | 5/2006 | Simon et al. | |
| 7,097,823 B2 | 8/2006 | Fritzberg et al. | |
| 2002/0131935 A1 | 9/2002 | Fisher et al. | |
| 2002/0133148 A1 | 9/2002 | Daniel et al. | |
| 2003/0118508 A1 | 6/2003 | Simon et al. | |
| 2004/0009955 A1 | 1/2004 | Larsen et al. | |
| 2004/0076582 A1 | 4/2004 | Dimatteo et al. | |
| 2004/0120890 A1 | 6/2004 | Dadachova | |
| 2004/0131543 A1 | 7/2004 | Wong et al. | |
| 2004/0228794 A1 | 11/2004 | Weller et al. | |
| 2004/0258614 A1 | 12/2004 | Line et al. | |
| 2005/0042753 A1 | 2/2005 | Yang et al. | |
| 2005/0085682 A1 | 4/2005 | Sasaki et al. | |
| 2005/0112061 A1 | 5/2005 | Holash et al. | |
| 2006/0003926 A1 | 1/2006 | Rajopadhye et al. | |
| 2006/0014938 A1 | 1/2006 | Groman et al. | |
| 2006/0067883 A1 | 3/2006 | Krom et al. | |
| 2007/0092440 A1 | 4/2007 | Braendle | |
| 2007/0196275 A1 | 8/2007 | Li et al. | |
| 2007/0196277 A1 | 8/2007 | Levin et al. | |
| 2007/0217998 A1 | 9/2007 | Wong | |
| 2007/0231329 A1 | 10/2007 | Lazar et al. | |
| 2007/0269375 A1 | 11/2007 | Chen et al. | |
| 2008/0193374 A1 | 8/2008 | Larsen et al. | |
| 2008/0226547 A1 | 9/2008 | Larsen et al. | |
| 2009/0028792 A1 | 1/2009 | Schwartz et al. | |

FOREIGN PATENT DOCUMENTS

| | | |
|---|---|---|
| EP | 0225409 | 6/1987 |
| EP | 0375376 | 6/1990 |
| EP | 0979656 | 2/2000 |
| EP | 2017253 | 1/2009 |
| WO | 97/49335 | 12/1997 |
| WO | 99/51277 | 10/1999 |
| WO | 00/43045 | 7/2000 |
| WO | 01/03745 | 1/2001 |
| WO | 03/051403 | 6/2003 |
| WO | 2004/050168 | 7/2004 |
| WO | 2004/067036 | 8/2004 |
| WO | 2005/016234 | 2/2005 |
| WO | 2005/061009 | 7/2005 |
| WO | 2006/059879 | 6/2006 |
| WO | 2007/085026 | 7/2007 |
| WO | 2007/126730 | 11/2007 |
| WO | 2008/060393 | 5/2008 |
| WO | 2008/103606 | 8/2008 |
| WO | 2008/151226 | 12/2008 |

(Continued)

OTHER PUBLICATIONS

Kinuya et al (Eur. J. Nucl. Med. Mol. Imaging, 2003, vol. 30, pp. 1246-1250).*
Gaze, et al., "Multi-modality megatherapy with metaiodoenzylguanidine." European Journal of Cancer, Feb. 1995: vol. 31A(2), pp. 252-256.
Hart, et al., "Antitumor Activity and Toxicity of Salts of Inorganic Group 111a Metals." PNAS, Jul. 1971, vol. 68(7): pp. 1623-1626.
Herzog, et al., "Measurement of Pharmacokinetics of Yttrium-86 Radiopharmaceuticals with PET." The Journal of Nuclear Medicine, Dec. 1993, vol. 34(12), pp. 2222-2226.
Sasaki, et al. "Clinical usefulness of FDG-PET in oncology." Nippon Igaku Hoshasen Gakkai Zasshi, Jul. 2001, vol. 61(8); pp. 414-420.
"Radiotherapy with Liquid Radioisotopes", Kahlson, et al., Acta-Unio Internationalis Contra Cancrum, vol. 20, pp. 1725-1727, 1964.
"Clinical Applications of Unsealed Radioisotopes", J. Sellars, Nursing Clinics of North America, vol. 2, No. 1, pp. 61-71, Mar. 1966.
"Radioactive colloidal solutions and suspensions for medical use", N.B. Mikheev, Atomic Energy Review, pp. 3-36, 1976.

(Continued)

*Primary Examiner* — D L Jones
(74) *Attorney, Agent, or Firm* — Vinson & Elkins LLP

(57) ABSTRACT

The present disclosure provides methods of using unsealed and non-colloidal radiopharmaceuticals, for example beta emitting radiopharmaceuticals such as Yttrium-90 chloride, Indium-111 chloride, F-18-2-deoxy-2-fluoro-D-glucose, or combinations thereof, for locoregional ablation of cells in the abnormal tissue.

55 Claims, 18 Drawing Sheets

FOREIGN PATENT DOCUMENTS

| | | |
|---|---|---|
| WO | 2009/045230 | 4/2009 |
| WO | 2009/059977 | 5/2009 |

OTHER PUBLICATIONS

"Phase II Study of Transarterial Holmium-166-Chitosan Complex Treatment in Patients with a Single, Large Hepatocellular Carcinoma", J. Shon et al., vol. 76, pp. 1-9, Nov. 17, 2008.

"Thyroid uptake of 131I: further comparisons of capsules and liquid preparations", J.P. Green, et al., Journal of Nuclear Medicine, pp. 310-312, 1976.

"Intracavitary administration of liquid radioisotopes", A.I. Malygina, et al., Meditsinkskaia Radiologiia, pp. 76-80, 1978.

"131-Iodine capsules in thyroid therapy: an individually controlled study of their uptake kinetics as compared to liquid 131-iodine", G.K. von Schulthess, et al., European Journal of Nuclear Medicine, vol. 10, pp. 25-28, 1985.

"Treatment of metastatic bone pain with strontium-89", R. Robinson, et al., Nucl. Med. Biol., vol. 14, No. 3, pp. 219-222, 1987.

"Clinical and Clinicopathologic Response of Canine Bone Tumor Patients to Treatment with Samarium-153-EDTMP", J. Lattimer, et al., Journal of Nuclear Medicine, vol. 31, No. 8, pp. 1316-1325, Aug. 1990.

"A different approach to the use of unsealed radionuclides for cancer therapy", V. McCready, European Journal of Nuclear Medicine, vol, 22, No. 1, pp. 1-3, Jan. 1995.

"Ultrasound-guided internal radiotherapy using yttrium-90-glass microspheres for liver malignancies", Tian, et al., Journal of Nuclear Medicine, vol. 37, No. 6, pp. 958-963, Jun. 1996.

"Intratumoral Injection of Rhenium-188 Microspheres into an Animal Model of Hepatoma", Wang, et al., Journal of Nuclear Medicine, vol. 39, No. 10, pp. 1752-1757, Oct. 1998.

"An early phase II study of intratumoral P-32 chromic phosphate injection therapy for patients with refractory solid tumors and solitary metastases", N. Firusian, et al., Cancer, vol. 85, No. 4, pp. 980-987, Feb. 1999.

"Thyroid uptake of liquid versus capsule 131I tracers in hyperthyroid patients treated with liquid 131I", J. Rini, et al., Thyroid, vol. 9, No. 4, pp. 347-352, 1999.

"A simple and rapid routine preparation of no-carrier added meta-I-123-and I-131-iodobenzylguanidine (I-123-MIBG and I-131-MIBG) for clinical nuclear medicine applications", S. Samnick, et al., Nulearmedizin, vol. 38, pp. 292-296, Jun. 1999.

"Stability of biodegradable radioactive rhenium (Re-186 and Re-188) microspheres after neutron-activation", U. Hafeli, et al., Applied Radiation and Isotopes, pp. 869-879, Jun. 2000.

"Pegylated liposomes have potential as vehicles for intratumoral and subcutaneous drug delivery", K. Harrington, et al., Clinical Cancer Research, vol. 6, pp. 2528-2537, Jun. 2000.

"Effects of Y-90-microspheres on liver tumors: Comparison of intratumoral injection method and intra-arterial injection method", Lin et al., Journal of Nuclear Medicine, vol. 41, No. 11, pp. 1892-1897, Nov. 2000.

"pH and therapy of human cancers", J. Evelhoch, Novartis Foundation Symposium, vol. 240, pp. 68-84, 2001.

"The potential of intratumoral unsealed radioactive source therapy", V. McCready, et al, European Journal of Nuclear Medicine, vol. 28, No. 5, pp. 567-569, May 2001.

"Effective local control of malignant melanoma by intratumoral injection of a beta-emitting radionuclide", J. Lee, et al., European Journal of Nuclear Medicine, vol. 29, No. 2, pp. 221-230, Feb. 2002.

"New approaches to the use of unsealed source radionuclide therapy for skeletal metastases" V. McCready, et al., Japanese Journal of Nuclear Medicine, vol. 39, No. 3, pp. 249-250, 2002.

"A model-based method for the prediction of whole-body absorbed dose and bone marrow toxicity for 186Re-IIEDP treatment of skeletal metastases from prostate cancer", F. Buffa, et al., European Journal of Nuclear Medicine and Molecular Imaging, vol. 30, No. 8, pp. 1114-1124, Aug. 2003.

"Stereotactic Injection of DTI-015 into Recurrent Malignant Gliomas: Phase I/II Trial", S. Hassenbusch, et al., Neoplasia, vol. 5, No. 1, pp. 9-16, Jan. 2003.

"DTI-015 Produces Cures in T9 Gliosarcoma", D. Pietronigro et al., Neoplasia, vol. 5, No. 1, pp. 17-22, Jan. 2003.

"An inflatable balloon catheter and liquid 125I radiation source (GliaSite Radiation Therapy System) for treatment of recurrent malignant glioma: multicenter safety and feasibility trial", S. Tatter, et al., Journal of Neurosurgery, vol. 99, pp. 297-303, Aug. 2003.

"Therapeutic Efficacy of DTI-015 using Diffusion Magnetic Resonance Imaging as an Early Surrogate Marker", D. Hall, et al., Clinical Cancer Research, vol. 10, pp. 7852-7859, Dec. 1, 2004.

"Therapeutic Effects of Holmium-166 Chitosan Complex in Rat Brain Tumor Model", R. Huh et al., Yonsei Medical Journal, vol. 46, No. 1,pp. 51-60, 2005.

"Biodistribution and excretion of radioactivity after the administration of Ho-166-chitosan complex (DW-166HC) into the prostate of rat", S. Seong, et al., European Journal of Nuclear Medicine and Molecular Imaging, vol. 32, No. 8, pp. 910-917, Aug. 2005.

"Teletherapy and Radiopharmaceutical Therapy of Painful Bone Metastases" E. Silberstein, MD, Seminars in Nuclear Medicine, pp. 152-158, 2005.

"Radionuclide therapy by direct intratumoural / intracystic approach", K. Tatsch, Annual Congress of the European Association of Nuclear Medicine, pp. 30-31, 2005.

"Complete tumor response following intratumoral P-32 BioSilicon on human hepatocellular and pancreatic carcinoma xenografts in nude mice", K. Zhang et al., Clinical Cancer Research, vol. 11, No. 20, pp. 7532-7537, Oct. 15, 2005.

"Preparation of a radionuclide/gel formulation for localised radiotherapy to a wide range of organs and tissues", O. Holte et al., Pharmazie, vol. 61, pp. 420-424, 2006.

"Long-term clinical outcome of phase IIb clinical trial of percutaneous injection with holmium-166/chitosan complex (Milican) for the treatment of small hepatocellular carcinoma", J. Kim, et al., Clinical Cancer Research, vol. 12, No. 2, pp. 543-548, Jan. 15, 2006.

"Enhanced antitumor effect of dendritic cell based immunotherapy after intratumoral injection of radionuclide Ho-166 against B16 melanoma", Lee et al., Immunology Letters, vol. 106, pp. 19-26, 2006.

"Intratumoral administration of rhenium-188-labeled pullulan acetate nanoparticles (PAN) in mice bearing CT-26 cancer cells for suppression of tumor growth", Song et al., Journal of Microbiology and Biotechnology, vol, 16, No. 10, pp. 1491-1498, 2006.

"Prospective Evaluation of Samarium-153-EDTMP Radionuclide Treatment for Bone Metastases in Patients with Honnone-Refractory Prostate Cancer", J. Dolezal et al., Urologia Internationalis, vol. 78, No. 1, 2 pages, 2007.

"Therapeutic Effects of a 186Re-Complex—Conjugated Bisphosphonate for the Palliation of Metastatic Bone Pain in an Animal Model", K. Ogawa et al., Journal of Nuclear Medicine, vol. 48, No. 1, pp. 122-127, Jan. 2007.

"Evaluation of chemical, physical, and biologic properties of tumor-targeting radioiodinated quinazolinone derivative", K. Wang et al., Bioconjugate Chemistry, vol. 18, pp. 754-764, Mar. 27, 2007.

"Levels and distribution of BCNU in GBN tumors following intratumoral injection of DTI-015 (BCNU-ethanol)", W. Bodell, et al., Neuro-Oncology, pp. 12-19, Jan. 2007.

"Synthesis of poly[APMA]-DOTA-Cu-64 conjugates for interventional radionuclide therapy of prostate cancer: Assessment of intratumoral retention by micro-positron emission tomography", J. Yuan et al., Molecular Imaging, vol. 6, No. 1, pp. 10-17, Jan. 2007.

"Liquid brachytherapy, direct administration of therapeutic isotopes into tumors", Journal of Nuclear Medicine, vol. 49, Supplement 1, pp. 1-2, 2008.

"Future directions for unsealed source radionuclide therapy for bone metastases", V. McCready, et al., European Journal of Nuclear Medicine, vol. 29, No. 10, pp. 1271-1275, Oct. 2002.

"Radiation dose distributions in normal tissue adjacent to tumors containing 131I or 90Y: The potential for toxicity", R. Sparks, et al., Journal of Nuclear Medicine, vol. 43, No. 8, pp. 1110-1114, Aug. 2002.

"American Cancer Society. Cancer Facts and Figures 2006", Atlanta: American Cancer Society, pp. 1-52, 2006.

"Preclinical Targeted Alpha Therapy for Subcutaneous Melanoma", Allen et al., Melanoma Research, vol. 11, pp. 175-182, 2001.

"Treatment of Patients with Advanced Cancer Utilizing Y-90 Microspheres", Blanchard et al., Cancer, vol. 18, pp. 375-380, Mar. 1965.

"Nonabsorbable Radioactive Material in the Treatment of Carcinomas by Local Injection", Nakhegevany et al., Cancer, vol. 61. pp. 931-940, Mar. 1, 1988.

"Beta-particle Dosimetry in Radiation Synovectomy", Johnson et al., European Journal of Nuclear Medicine, vol. 22, No. 9, pp. 977-988, Sep. 1995.

"Biodistribution and Kinetics of Ho-166-Chitosan Complex in Rats and Mice", Suzuki et al., Journal of Nuclear Medicine, vol. 39, No. 12, pp. 2161-2166, Dec. 1998.

"In Vivo Studies of Pharmacokinetics and Efficacy of Bismuth-213 Labeled Antimelanoma Monoclonal Antibody 9.2.27", Rizvi et al., Cancer Biology & Therapy, vol. 4, issue 7, pp. 763-768, Jul. 2005.

"Intralesional Targeted Alpha Therapy for Metastatic Melanoma", Allen et al., Cancer Biology & Therapy, vol. 4, issue 12, pp. 1318-1324, Dec. 2005.

"Yttrium-90 Microsphere Selective Internal Radiation Treatment of Heaptic Colorectal Metastases", Gulec et al., Arch. Surg., vol. 142, No. 7, pp. 675-682, Jul. 2007.

* cited by examiner

LOCOREGIONAL INTERNAL RADIONUCLIDE ABLATION OF ABNORMAL TISSUES

CROSS REFERENCE TO RELATED APPLICATION

This application is a continuation of PCT/US05/31396 filed Sep. 2, 2005 which claims benefit of 60/607,052 filed Sep. 3, 2004.

STATEMENT REGARDING FEDERALLY SPONSORED RESEARCH OR DEVELOPMENT

The U.S. Government may have certain rights in this invention because part of the work performed during development of this disclosure utilized U.S. Government funds. Part of the work described in this disclosure was supported by U.S. Army Medical and Material Command, DOD Breast Cancer Research Program grant BC020808, which was awarded to Dr. Franklin C. Wong at M. D. Anderson.

REFERENCE TO A "Microfiche Appendix"

Not applicable.

BACKGROUND OF THE INVENTION

1. Field of the Invention

The present disclosure relates to methods for the treatment of abnormal tissues using radionuclide compounds.

2. Description of Related Art

Radiation therapy has been used with some success in treating tumors and other diseases, and can be an effective therapeutic alternative. Radiotherapeutic agents include radionuclides with alpha or energetic beta emissions that can be targeted to disease sites. For example, one therapeutic use of these radiotherapeutic agents is for the locoregional ablation of cancerous cells or tumors. Optimal radiotherapeutic agents deposit sufficient radioactivity in target tissues to kill abnormal or targeted cells while minimizing uptake in non-target tissues. Therefore, it is generally understood that the effective dose of radiation must be sufficiently limited to the tumor or other target tissue to avoid injuring the surrounding tissues and the overall health of the patient. Currently, only a few radiopharmaceutical particles are available for locoregional treatment of cancerous cells or tumors, such as FDA approved Y-90 particles (Sir-Spheres®) (U.S. Pat. Nos. 6,537,518, 6,258,338 and 5,885,547; Keng et al., (2003) *Ann. Acad. Med. Singapore* 32(4):518-524; Sarfaraz et al., (2003) *Med. Phys.* 30(2):199-203).

Directed local treatment of cancer can be achieved by implanting sealed radiation sources into, for example, a post-surgical field for several weeks. Conventional brachytherapy involves the implantation of sealed radiation sources into the post-surgical field for several weeks (Nag et al., (2001) *Oncology* 15:195-202). Additionally, clinical trials have reported favorable outcomes for treating brain and breast cancer patients using a single implanted catheter filled with Iodine-125 Iotrex and Iridium-192 seeds irradiating the tissues around the post-surgical cavity (Proxima Therapeutices, Inc.) (King et al., (2000) *Amer J Surg* 180:299-304; Vicini et al., (2002) *J Clin Oncol* 19:1993). This approach has gained FDA approval, for example GlialSite for brain tumors and MammoSite for breast cancer (deGuzman et al., (2000) *J Nucl Med* 41 (5 Suppl):274P; Dempsey et al., (1998) *Int J Radiat Oncol Biol Phys* 42:421-29). Local irradiation of breast cancer using the sealed radioisotope Iridium-192 contained in an inflatable balloon is also an established approach to breast-conservation therapy in patients (Keisch et al., (2003) *Int. J. Radiat. Oncol. Biol. Phys.* 55(2):289-293; Streeter et al., (2003) *Breast* 12(6):491-96). This method requires, however, additional surgeries to implant and explant the Iridium-192 device. While these FDA approved approaches illustrate the desirable features of locoregional radionuclide therapy, a more desirable approach would be to directly ablate tumors using, for example, intratumoral injection of readily available radionuclides, without requiring surgical procedures to remove the radiation source(s).

Thus, it is highly desirable to identify a radiopharmaceutical that can be used for locoregional treatment of abnormal tissues, for example a solid tumor or the surrounding tissues after the tumor is removed, which does not require undesirable and tedious steps for synthesizing the radiopharmaceutical, surgical implantation or other more invasive procedures to deliver the radiopharmaceutical to the subject, or invasive procedures to remove the radiation sources(s).

BRIEF SUMMARY OF THE INVENTION

The present disclosure is directed to locoregional or local introduction of unsealed and non-colloidal radiopharmaceuticals in the region of the abnormal tissue or cells of a subject, wherein the radiopharmaceutical has sufficient radioactivity for locoregional ablation of the abnormal tissue or cells. Surprisingly, these radiopharmaceuticals are generally locally sequestered after introduction into abnormal tissue or cells, rather than simply diffusing away from the site of introduction. Alternatively, these radiopharmaceuticals deliver sufficient radioactivity for locoregional ablation of abnormal tissue or cells before diffusing away from the site of introduction. The use of these radiopharmaceuticals instead of sealed or colloidal radiopharmaceuticals offers several advantages, including the ready availability and established toxicity of these radiopharmaceuticals, as well as rendering the implantation and explantation procedures associated with the use of sealed radiopharmaceuticals unnecessary. In addition, these radiopharmaceuticals are available with varying half-lives and biological clearance properties, which may be used to optimize therapeutic treatments.

Preferred embodiment of the present disclosure are directed to methods for the locoregional treatment of abnormal cells or tissue in a subject comprising administering an effective amount of a radiopharmaceutical to the subject in the region of the abnormal tissue for locoregional ablation of cells in the abnormal tissue. In certain embodiments the radiopharmaceutical is locally sequestered after introduction into the abnormal tissue, while in other embodiments the radiopharmaceutical comprises an effective amount of radioactivity for locoregional ablation of cells in the abnormal tissue before diffusing away from the site of administration. Other embodiments are directed to methods for the locoregional treatment of tissues surrounding a post-surgical cavity, comprising administering an unsealed and non-colloidal radiopharmaceutical to tissues surrounding a post-surgical cavity in a subject. Preferably the radiation absorbed doses from the radiopharmaceutical will be high within the abnormal tissue or cells to ablate abnormal cells, but low in surrounding tissues and body organs, thereby reducing the toxicity of the radiopharmaceutical to the subject.

Preferably the radiopharmaceutical administered for locoregional ablation of abnormal tissues or cells as disclosed herein is Indium-111 chloride ($^{111}$In—Cl), Yttrium-90 chloride ($YCl_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP($^{166}$Ho-DOTMP), Samarium-153 EDTMP ($^{153}$Sm-EDTMP), F-18-2-deoxy-2-fluoro-D-glucose (F-18 FDG), or an Iodine-131 labeled soluble compound (e.g., iododeoxyuridine, meta-iodobenzylguanidine, or iodocholesterol (NP59), and the like), or combinations thereof. Preferred combinations of radiopharmaceuticals are $^{111}$In—Cl and YCl$_3$, $^{111}$In—Cl and F-18 FDG, and F-18 FDG and YCl$_3$, and may be administered together or separately. Other than for F-18 FDG, the presence of the free radioactive metal ions In-111, Y-90, Cu-61, Cu-62, Cu-64, Ga-68, Ga-67, Ga-66, Ho-166, or Sm-153 will be preferably sufficient to deliver the ablative power. Preferably, the radiopharmaceutical emits beta radiation, gamma radiation, and/or positrons.

In preferred embodiments, the radiopharmaceutical is administered to a subject, wherein the subject is a vertebrate, more preferably the subject is a mammal, and most preferably the subject is a human. In preferred embodiments, the radiopharmaceutical is administered in proximity or directly to abnormal tissues or cells in the subject, for example neoplastic tissues such as a tumor, or tissues surrounding post-surgical cavities in which there are unresectable micrometastases. In certain embodiments, the radiopharmaceutical is administered directly into the abnormal tissue or tumor, for example by injection. In other embodiments, the radiopharmaceutical is injected into the subject in a saline solution, with the pH of the solution preferably being from about 2.0 to about 12.0, more preferably from about 8.0 to about 10.0, and most preferably from about 4.0 to about 6.0.

Preferably, while the radiopharmaceutical disperses after injection, it remains largely contained within the abnormal tissue or cells. The radiopharmaceutical may be administered by injection, for example interstitial, intralesional, intramuscular, intracavitary, intrathecal, or intratumoral injection. The radiopharmaceutical may be injected at a single location, or multiple locoregional injections may be used in different locations in the same subject, for example, there may be multiple injection sites in a single tumor or targeted tissue. If multiple injections of the radiopharmaceutical are administered to a subject, they may be given at the same time, or over a period of time (e.g., fractionation), for effective treatment. In other embodiments, the radiopharmaceutical is administered with an effective amount of a radiosensitizer to the abnormal tissue, for example 2-deoxy-D-glucose (2DG). The radiosensitizer may be given at the same time or after administration of the radiopharmaceutical, but is preferably administered before administration of the radiopharmaceutical.

In other embodiments of the present disclosure, the radiopharmaceutical is used for radiosynoviorthesis, for example to ablate synovial tissue. In some embodiments, the radiopharmaceutical is administered directly into the synovial tissue. In other embodiments, magnetic resonance imaging (MRI), Positron Emission Tomography (PET), Computed Tomography (CT) scanner, single photon emission computed tomography (SPECT), ultrasonography, and/or high resolution gamma scintigraphy are used to measure the spatial and temporal profiles of the radiopharmaceutical after administration, either immediately or after delayed periods of time, for example up to several days.

In certain embodiments of the present disclosure, two or more radiopharmaceuticals disclosed herein can be administered together to provide a spectrum range for ablating abnormal tissues or cells. For example, a radiopharmaceutical for the locoregional treatment of abnormal tissue may comprise a combination of two or more radiopharmaceuticals, such as Indium-111 chloride ($^{111}$In—Cl) and Yttrium-90 chloride (YCl$_3$), Indium-111 chloride ($^{111}$In—Cl) and F-18-2-deoxy-2-fluoro-D-glucose (F-18 FDG), or F-18-2-deoxy-2-fluoro-D-glucose (F-18 FDG) and Yttrium-90 chloride (YCl$_3$), wherein the radiopharmaceutical has sufficient radioactivity for locoregional ablation of cells in the abnormal tissue.

BRIEF DESCRIPTION OF THE SEVERAL VIEWS OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
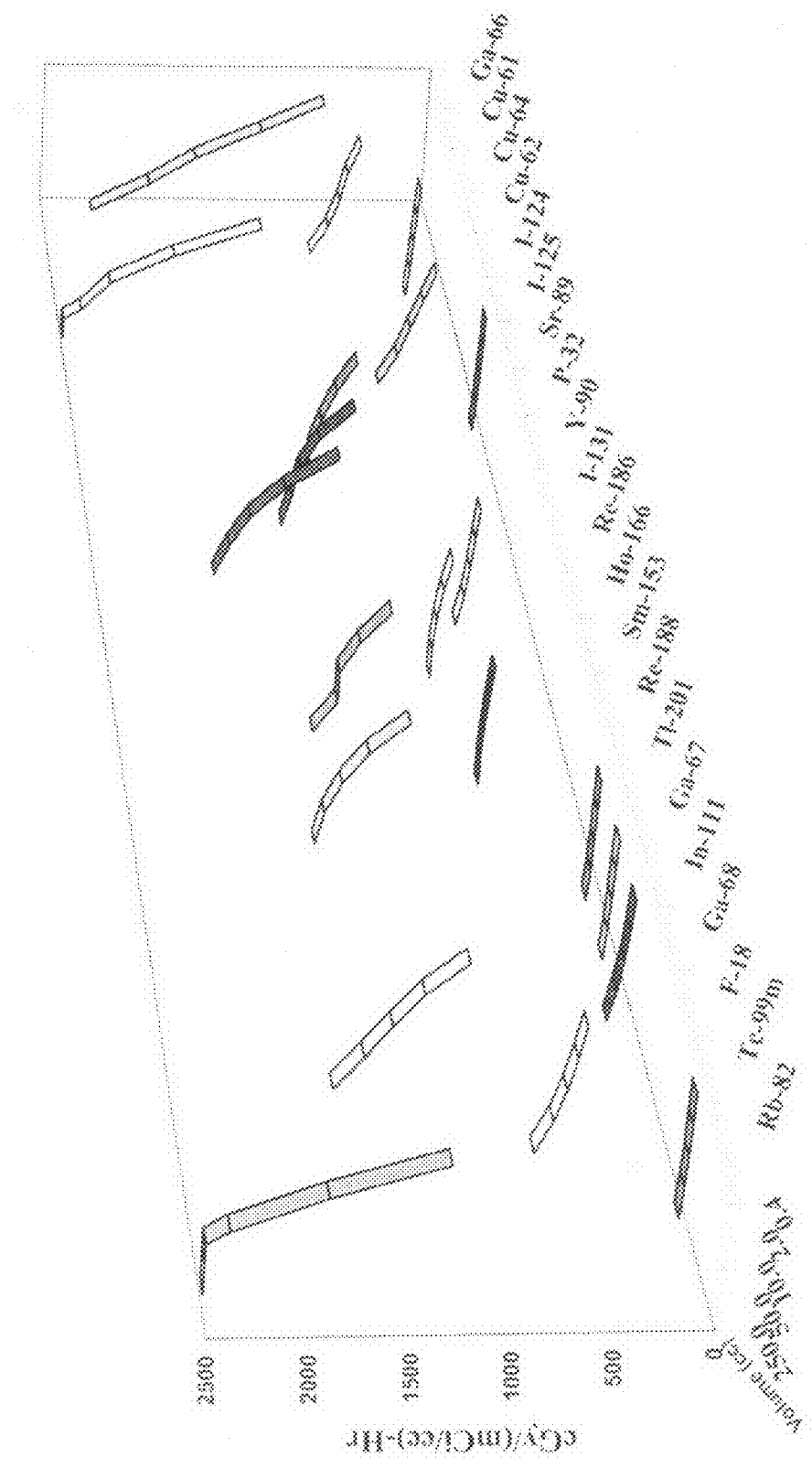
FIG. 1. Diagram of the normalized S-values inside the 5 spheres of volumes of 0.4 cc, 2 cc, 10 cc, 50 cc, and 250 cc from Monte Carlo Simulation of gamma and beta emissions.

The present disclosure is directed to the surprising use of unsealed and non-colloidal radiopharmaceuticals for locoregional ablation of cells in abnormal tissue or cells of a subject. The radiopharmaceuticals useful in the present disclosure include but are not limited to soluble radiopharmaceuticals or aqueous solutions of the radiopharmaceuticals, with or without admixture with soluble paramagnetic/supramagnetic properties, nanocolloids for MRI, non-radioactive contrast materials for CT, or microparticles for ultrasonography. Preferably, the radiopharmaceuticals useful in the methods of the present disclosure are small molecules, for example, molecules below 10,000 Daltons. Unexpectedly, these radiopharmaceuticals are generally locally sequestered after introduction in proximity to or directly to abnormal tissue or cells, or deliver sufficient radioactivity for locoregional ablation of abnormal tissue or cells before diffusing away from the site of introduction. Thus, these radiopharmaceuticals may be used for nonspecific ablation when administered to abnormal tissues or cells, for example by interstitial, intralesional, intrathecal, intramuscular, or intratumoral injection, or other means of locoregional targeting known to those of skill in the art.

These radiopharmaceuticals may be used for locoregional ablation of abnormal tissues, preferably neoplastic tissues, cancerous tissues, tumors, synovial tissues, or tissues surrounding a surgical resection site, for example the surgical resection site of a solid tumor wherein micrometastases of the tumor reside. In preferred embodiments, while these radiopharmaceuticals may disperse into the tissues or cells upon administration, they will be primarily retained in the targeted tissues or cavities for sufficient duration for irradiation. The sufficiency of such duration is determined by the derived radiation dosimetry (by model) of each radiopharmaceutical or radionuclide. In addition, the greater dispersion of these radiopharmaceuticals may offer a more generalized treatment of abnormal tissues or cells, particularly when compared to the more focal treatment achieved by using radioactive colloidal particles or macroaggregate radiopharmaceuticals.

For example, a radiopharmaceutical disclosed herein injected into breast tissue will disperse in the breast tissue, but will preferably remain largely contained within a fixed volume surrounding the tissue, leading to high absorption of radiation within the breast tissue from the radiopharmaceutical, but low radiation absorption in tissues outside of that volume and other organs. The radiopharmaceuticals of the present disclosure may also be used to therapeutically treat a subject with a tumor that has already been irradiated but has subsequently recurred locally, when the surrounding healthy tissue should not be exposed to further external beam radiation. In another embodiment, these radiopharmaceuticals may be used to initially treat or downstage inoperable tumors, or to prevent recurrence of tumors after resection.

This simple approach of using available radiopharmaceuticals with well established toxicity profiles as major components of the injectate will alleviate the many undesirable and tedious steps for chemically synthesizing specialized or sealed radiopharmaceuticals, and the larger volume of distribution of the radiopharmaceuticals may also partly overcome the heterogeneous distribution problems that are potential pitfalls of using radiocolloids. Another significant advantage of using the presently disclosed radiopharmaceuticals for therapeutic applications is that they render unnecessary the implantation and explantation procedures associated with the use of sealed radiopharmaceuticals in a subject. In addition, these radiopharmaceuticals generally have low systemic toxicity, and are readily available with varying half-lives and biological clearance properties to optimize therapeutic treatments. As used herein, the terms "radiopharmaceutical," "radioactive isotope" and "radionuclide" are used interchangeably.

Preferably the unsealed or non-colloidal radiopharmaceutical utilized in the present disclosure is Indium-111 chloride ($^{111}$In—Cl), Yttrium-90 chloride (YCl$_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP($^{166}$Ho-DOTMP), Samarium-153 EDTMP ($^{153}$Sm-EDTMP), F-18-2-deoxy-2-fluoro-D-glucose (F-18 FDG), or an Iodine-131 labeled soluble compound (e.g., iododeoxyuridine, meta-iodobenzylguanidine, or iodocholesterol (NP59), and the like), or various combinations of these radiopharmaceuticals. Preferably the radiopharmaceutical emits beta radiation, alpha radiation, gamma radiation, and/or positrons, and may be either the cationic and anionic species of the radionuclide. Important properties of the radioactive isotopes that may be used in the present disclosure are set forth below in Table 1:

TABLE 1

| Radionuclide | Half-Life | Principal Gammas (MeV) | Principal Betas (MeV) | Principal Positrons (MeV) |
|---|---|---|---|---|
| In-111 | 68 hours | 0.245 | 0.002 | |
| Y-90 | 64 hours | | 2.284 | |
| Cu-61 | 3.4 hours | | | 1.216 |
| Cu-64 | 12.7 hours | | 0.578 | 0.653 |
| Ga-66 | 9.49 hours | 1.03 | | 4.153 |
| Ga-67 | 78 hours | 0.093 | 0.008 | |
| Ga-68 | 68 minutes | | | 1.900 |
| F-18 FDG | 109.8 min. | | | 0.250 |

$^{111}$In—Cl is a desirable radiopharmaceutical for use in the present disclosure because it is generally locally sequestered after introduction in proximity to or directly to abnormal tissue or cells, and emits gamma radiation that is effective for ablation of abnormal tissue or cells. In addition, $^{111}$In—Cl can be clinically imaged with a gamma camera, and intravenous $^{111}$In—Cl was used in human bone marrow imaging in the 1970s, so its systemic toxicity profiles have been established (Jeffcoat et al., (1978) *J. Nucl. Med.* 19:496-500) and can serve as a ceiling of toxicity for the locoregional administration of $^{111}$In—Cl. YCl$_3$ is also a desirable radiopharmaceutical for use in the present disclosure because it is readily available, and Yttrium-90 emits beta radiation which is effective for ablation of abnormal tissue or cells. Although some mortality was observed after locoregional administration of YCl$_3$ in rats, it occurred at high dose equivalents for human (350 mCi/70 Kg). While this level suggests that there will be a ceiling for YCl$_3$ administration to humans, local tumor suppression effects have been consistently observed with doses as low as 0.2 mCi, indicating a large therapeutic window for the administration of YCl$_3$.

Other desirable radiopharmaceuticals such as $^{68}$Ga—Cl can be obtained from a $^{68}$Ge—$^{68}$Ga generator that is commercially available, while $^{67}$Ga—Cl can be synthesized by precipitating commercially available $^{67}$Ga citrate with FeCl$_3$, and redissolving the precipitate in hydrochloride acid. $^{66}$Ga, $^{61}$Cu, and $^{64}$Cu are cyclotron products with half-lives that are sufficiently long enough to allow them to be transported to neighboring laboratories, but not too long to cause serious radiation disposal concerns for unused or excreted isotopes.

F-18 FDG has been shown to be sufficient to induce apoptosis in rat breast cancer after systemic injection, while also having low toxicity (Mortimer and Taylor, (2003) *Breast Cancer Res.* 5(6):329-331; Moadel et al., (2003) *Breast Cancer Res.* 5(6):R199-R205, each incorporated herein by reference). Locoregional injection of F-18 FDG will deliver greater than 100 times the positron dose directly to the abnormal tissues or cells. Advantages of intratumoral/locoregional injection of F-18 FDG are that it has low systemic radiotoxicity, and safety guidelines for this radiopharmaceutical have already been established (up to 25 mCi systemic dose). In addition, F-18 FDG may be readily monitored and quantified using PET procedures to establish efficacy and safety of locoregional administration, and may also be useful for imaging-guided targeted radionuclide therapy. For example, the distribution of F-18 FDG may be measure by PET, or any other methods disclosed herein.

Surprisingly, a dramatic increase in tumor suppression by $^{111}$In—Cl was observed as the injection volume but not the therapeutic dosage of the radiopharmaceutical was increased. Thus, for certain treatments of abnormal tissue or cells of a subject with the disclosed radiopharmaceuticals, for example treatment of post-surgical peri-cavity tissues for micrometastases to prevent recurrence of abnormal tissues or cells, larger volumes of injectate will be utilized. These larger volumes of injectate will have a larger volume of distribution upon introduction into the subject, but will also have a lower radiation dose to minimize toxicity to the subject. The volume of injectate can be upscaled from about 1, 2, 3, 4, 5, 10, 15, 20, 25, 30, 35, 40, 45, 50, 75, or 100 cc to about 150, 200, 250, 300, 350, 400, 450, 500, 550, 600, 650, 700, 750, 800, 850, 900, 950, or 1000 cc (about 1 liter). In other preferred embodiments, the dose penetration of the larger volumes of injectate will cover a large portion of the residual cavity, tissue, or organ, or cover long depths of area surrounding the targeted cavity, tissue, or organ. For example, the volume of injectate will preferably cover at least about 30%, 40%, 50%, 60%, 70%, 80%, 90%, 95%, or 99% of the residual cavity, tissue, or organ, or will preferably cover depths with about a 0.5 to 2 cm margin beyond the targeted cavity, tissue, or organ, more preferably about a 1.0 to 1.5 cm margin beyond the targeted cavity, tissue, or organ. Radiation dosimetry profiles for these injectate volumes can be predicted by the disclosed Monte Carlo Dosimetry models (FIG. 1) both inside and outside of the injectate.

After administration of the radiopharmaceuticals as disclosed herein, nuclear imaging, scintigrams, and magnetic resonance imaging may be used to derive the temporal course and high-resolution spatial distribution of the radiopharmaceutical to allow construction of radiation dosimetry profiles. For example, magnetic resonance imaging (MRI), Positron Emission Tomography (PET) (e.g., PET/CT scanners from GE or Siemens, or animal PET using a Concord Micro-PET (R4) camera for rodents), Single Photon Emission Computed Tomography (SPECT), ultrasonography, Computed Tomography (CT) scanner, and/or high resolution gamma scintigraphy (e.g., using Gamma cameras from GE or Siemens, or Seimens M-cam for animals) may be used to measure the spatial and temporal profiles of the radiopharmaceutical after introduction into a subject, and to determine the effective half-life, biological half-life, and residence time of the radiopharmaceutical in vivo. Preferably, the pharmacokinetic data generated using such techniques combined with nuclear imaging is used to calculate whole-body, organ, and locoregional radiation dosimetry to evaluate the safety and efficacy factors for a specific radiopharmaceutical.

The clearance of foreign substances from tissues depends on many factors, such as the return of small molecules below 10,000 Daltons to systemic circulation via capillary blood flow, lymphatic drainage for larger molecules above 10,000 Daltons, and phagocytosis by macrophages of other particles. The initial volume of distribution of the radiopharmaceutical injectates disclosed herein may also be estimated by co-injection of the radiopharmaceuticals with other imaging agents, which are then imaged before significant drainage occurs. For example, initial physical distribution around the administration site of the disclosed radiopharmaceuticals may be estimated by using admixtures or co-injecting with available non-radioactive imaging agents such as iron-containing or gadolinium-containing compounds (e.g., FeCl$_3$, Fe-DTPA, Fe-nanocolliods, $GdCl_3$, Gd-DTPA (Magnevist®), or Ferindex), iodine-containing compounds, MRI contrast agents, CT contrast agents, or ultrasound contrast agents, all of which are well known to those of skill in the art. These non-radioactive imaging agents will, via non-radioactive imaging devices such as MRI, CT, PET, SPECT, or ultrasound, provide volumetric information for administered radiopharmaceuticals, which preferably distribute concurrently with the non-radioactive imaging agents. Use of these admixtures or co-injections is particularly preferred when the estimation of distribution volume is suboptimal by scintigraphy. This volumetric information can be the bases for dosimetric calculations to quantify the ablation effects of the radiopharmaceuticals disclosed herein. Gamma/PET imaging, as well the non-radioactive imaging, may also allow imaging-guided targeting for the treatment of abnormal tissues.

In certain embodiments of the present disclosure, two or more therapeutic radionuclides disclosed herein with various half-lives and ranges can be administered together to provide a spectrum range for ablating abnormal tissues or cells. In one preferred embodiment, a radionuclide that can be monitored is administered or combined with a radionuclide that will ablate tissue and cells in proximity with the radionuclide. For example, $^{111}$In—Cl may be administered with another radionuclide such as $YCl_3$, with $^{111}$In—Cl primarily available for monitoring and $YCl_3$ primarily available for therapeutic ablation of abnormal tissue or cells. In a preferred embodiment, about 0.1 to about 10 mCi $^{111}$In—Cl is administered for monitoring and targeted ablation of abnormal tissue or cells. In addition, 90Y at higher radioactivity levels (>0.2 mCi in 0.5 cc) emits sufficient Bemstraulung (gamma) radiations that its distribution can be monitored by gamma cameras. In a preferred embodiment, about 0.1 to about 100 mCi of $YCl_3$ is administered for monitoring and targeted ablation of abnormal tissue or cells. If a combination of radiopharmaceuticals are administered to a subject, they may be administered together or separately, either at the same time or appropriately spaced in time to maximize the therapeutic benefit to the subject.

While not wishing to be bound to any particular theory, experimental evidence suggests that certain radiopharmaceuticals such as $^{111}$In—Cl are unexpectedly locally sequestered, rather than diffusing away from the site of administration, through protein binding, for example by binding serum proteins or structural proteins, in the administration site and adjacent cells and tissues (Raijmakers et al., (1992) *Nucl. Med. Comm.* 13:349-356; Hosain et al., (1969) *Clin. Chim. Acta* 24:69-75; Castronovo et al., (1973) *J. Nucl. Med.* 14:677-682, each incorporated herein by reference). Binding of the In-111 cation of $^{111}$In—Cl to serum proteins or structural proteins may prevent their immediate clearance from the site of administration and serve as the basis for the presently observed sequestration of this radiopharmaceutical, thereby allowing locoregional ablation of surrounding cells and tissues. When this binding occurs, for example in the interstitium, the radiopharmaceutical is sequestered, thereby resulting in ablation of abnormal tissue or cells in proximity to the radiopharmaceutical. In fact, as long as the radiopharmaceuticals are retained for sufficient duration to deliver the radiation locally, the mechanism of retention is less relevant for nonspecific ablation. The sufficiency of such duration is determined by the radiation dosimetry, which in turn is determined by the nature of the emitted radiation and the physical distribution of the injection.

In other preferred embodiments, the radiopharmaceuticals disclosed herein to therapeutically treat a subject can be combined with other therapeutic alternatives well known to those of skill in the art for treating neoplasms or other abnormal tissues. The other therapeutic alternatives include but are not limited to chemotherapy, surgery, external radiotherapy, pharmacotherapy, hormone therapy, gene therapy, radioimmunotherapy, immunotherapy, radiosensitizers, and the like (R.C. Bast, Ed. Cancer Medicine. 5th Ed. American Cancer Society, B. C. Decker, 2000, incorporated herein by reference).

For example, radiopharmaceuticals disclosed herein may be administered with a radiosensitizer to potentiate the therapeutic effect of the radiopharmaceutical. A radiosensitizer is a drug that enhances the effect of radiation treatment in a subject, and may be administered through locoregional targeting or systemic administration. The use of a radiosensitizer (e.g., Texaphyrin, Rhodamine, BUDR), whether non-radioactive or radioactive, along with radiotherapy has been found to increase tumor cell killings several fold (e.g., Teicher et al., (1987) *Int. J. Radiat. Oncol. Biol. Phys.* 13:1217-24, incorporated herein by reference). However, the systemic use of radiosensitizers is limited by low regional delivery and systemic toxicities such as hepatic and dermatologic toxicity. On the other hand, locoregional application of radiosensitizers along with locoregional radionuclide therapy with radiopharmaceuticals disclosed herein will exploit pharmacokinetic advantages because of the initial exposure of the abnormal tissue or cells to 100% of the radiosensitizer. Any of the above therapeutic alternatives may be used before, with, or after locoregional application of the radiopharmaceutical to achieve enhanced locoregional ablation and cell kills.

In certain embodiments of the present disclosure, each or any combination of the radiopharmaceuticals disclosed herein may be administered with non-radioactive radiosensitizers to enhance the therapeutic effects of the radiopharmaceuticals. For example, up to a 20 mg/kg systemic dose of 2-deoxy-D-glucose (2DG) has been found to be effective in enhancing the effects of a radiopharmaceutical, and 2DG has low toxicity with established profiles in Phase I and Phase II clinical trials (Kalia, (1999) *Indian J. Med. Res.* 109:182-187; Mohanti et al., (1996) *Int. J. Radiat. Oncol. Biol. Phys.* 35(1): 103-111, each incorporated herein by reference). An advantage to administering 2DG with, for example, F-18 FDG, is that they share the same metabolic pathways (Sokoloff, (1981) *J Cereb. Blood Flow Metab.* 1:7-36). Therefore, the distribution of F-18 FDG should directly reflect that of 2DG, which will allow for better quantification of the effects of radiation sensitization.

In another example, the radiopharmaceuticals disclosed herein may be administered in combination with Rhodamine-123 (Rh-123). Rh-123 is a cationic, lipophilic, water-soluble oxonium chloride salt with a high affinity for the mitochondria of malignant cells. Rh-123 has been found to be selectively toxic to a number of human cancer cell lines. In a preferred embodiment, a powder form of Rh-123 is used, and the Rh-123 will function after local injection as a slow-releasing deposit radiosensitizer, which coincides with the radioactive life of the radiopharmaceutical. In another preferred embodiment, a saturated solution of Rh-123 is used for locoregional injection.

Alternatively, systemic toxicity to a subject resulting from administration of the radiopharmaceuticals disclosed herein may be reduced by systemic treatment/salvage with, for example, compounds that capture radiometals when administered to the subject. Examples of systemic salvage are well known to those of skill in the art, and include, for example, the administration of Calcium-DTPA (Trisodium calcium diethylenetriaminepentaacetate), Zinc-DTPA, or non-radioactive Iodine to the subject before, during, or after administration of the radiopharmaceutical. For example, a subject may be systemically treated with non-radioactive Ca DTPA (up to the human equivalent of 1 gram per day), which is an FDA approved drug. While not wishing to be bound to any particular theory, systemic administration of Ca DTPA may eliminate inadvertent internal accumulation of radiometals in the subject, as well as protect a subject from whole-body exposure to the radioactive metals used, such as $YCl_3$ or $^{111}$In—Cl. Locoregional treatment with the disclosed radiopharmaceuticals combined with systemic protection may be more effective in treating abnormal tissues such as tumors. For additional information on Ca DTPA, see Breitenstein et al., "DTPA therapy: The U.S. Experience 1958-1987," in: The Medical Basis of Radiation Accident Preparedness, 2nd ed., Elsevier Science Publishing Co., Inc., pp. 397-406, 1990, incorporated herein by reference.

In another embodiment of the present disclosure, admixtures of the disclosed radiopharmaceuticals, for example $^{111}$In—Cl, $YCl_3$, $^{67}$Ga—Cl, or $^{67}$Ga citrate, with free iron (e.g. $FeCl_3 \cdot 6H_2O$ at 1-5 mg Fe/ml) have a markedly prolonged retention of radioactivity after locoregional injection. Therefore, in certain embodiments, each or any combination of the radiopharmaceuticals disclosed herein may be co-administered with free iron (e.g., $FeCl_3$, hydrated $FeCl_3$, Ferrous, $FeCl_2$, $FeSO_4$, $Fe(SO_4)_3$, or $Fe(NO_3)_3$), which increases the retention of the radiopharmaceuticals at the site of administration. In other alternative embodiments, each or any combination of the radiopharmaceuticals disclosed herein may be co-administered with epinephrine, for example at 1:100,000 to 1:25,000 levels, again to increase the retention of the radiopharmaceuticals at the site of administration. Increasing local retention of the radiopharmaceuticals preferably enhances locoregional treatment of abnormal tissues.

Such combinations/admixtures may serve a double-modality for imaging purposes, i.e., MRI images may be used to detect the iron distribution of the combinations/admixtures, which is presumed to be identical to the distribution of the radionuclide in the combinations/admixtures. Therefore, the co-administration of free iron may serve a dual purpose: 1) to provide paramagnetic signals for detection of the distribution of the injectate; and 2) to provide an environment that allows for prolonged retention of the radionuclide in the locoregional injection site. The volume of soluble radiopharmaceuticals may also be determined by the co-administration of other compounds such as Ferrindex (Fe oxide nanoparticles), gadolinium chloride (Gd—$Cl_3$), Gd-DTPA (Megavist), and non-radioactive sodium iodide (1-127 NAI). For example, I-127 NAI may be co-administered with a radiopharmaceutical at 1-200 mg 1-127 NAI content/ml to allow CT measurement of the initial volume of the injectate. Monitoring the temporal and spatial dispersion of the radiopharmaceuticals disclosed herein may also allow for more accurate image-guided locoregional treatment of abnormal tissues. In addition, recent advances in SPECT/CT and PET instrumentation in medical imaging will aid this methodology (See Seo et al., (2005) *J Nucl. Med.* 46(5):868-77; Sachelarie et al., (2005) *Oncology* 19(4):481-496).

In still another embodiment of the present disclosure, the radiopharmaceuticals utilized in the methods disclosed herein are radiolabeled blood elements, for example radiolabeled serum proteins (e.g., albumin or transferin), red blood cells, white blood cells, or platelets. Thus, a radiolabeled blood element may be used for the locoregional treatment of abnormal tissue or cells. Although some blood elements are soluble, they are relatively large molecules that will be cleared slowly from the injection site. Alternatively, the blood elements may aggregate at the injection site, for example in a tumor. Preferably, the blood elements are radiolabeled with a radionuclide that has sufficient ablative power, selected from the following group: In-111, Y-90, Cu-61, Cu-62, Cu-64, Ga-68, Ga-67, Ga-66, 1-131, 1-124, F-18 FDG, Re-188, Re-186, Ho-166, or Sm-153. Preferably the radiolabeled blood element emits beta radiation, gamma radiation, and/or positrons.

Preferably the radiopharmaceuticals disclosed herein emit beta radiation, alpha radiation, and/or positrons sufficient to ablate abnormal cells, and may or may not emit gamma rays. In other preferred embodiments, the radiopharmaceutical emits radiation of high energy and short range, for example photons, beta particles, or other therapeutic rays. In preferred embodiments, the radiopharmaceutical yields about 80-99% radioactivity that is stable in saline (e.g., phosphate buffer saline) over at least 24 hours. In other preferred embodiments, the unsealed radiopharmaceutical yields about 81%, 82%, 83%, 84%, 85%, 86%, 87%, 88%, 89%, 90%, 91%, 92%, 93%, 94%, 95%, 96%, 97%, or 98% radioactivity that is stable in saline over at least 24 hours. In some embodiments, the radiopharmaceutical administered to the subject is in a solution, for example saline, with a pH of about 2.0 to about 14.0, more preferably from about 4.0 to about 7.0. In other embodiments, the pH of the solution is about 2.5, 3.0, 3.5, 4.5, 5.0, 5.5, 6.5, 7.0, 7.5, 8.0, 8.5, 9.0, 9.5, 10.5, 11.0, 11.5, 12.0, 12.5, 13.0, or 13.5.

In other preferred embodiments, the therapeutic dosage range of the radiopharmaceutical disclosed herein is from about 0.1 microcurie (µCi) to about 500 mCi, more preferably about 1, 5, 10, 20, 30, 40, 50, 60, 70, 80, 90, 100, 150, 200, 250, 300, 350 400, 450, or 500 µCi to about 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, or 450 mCi. In preferred embodiments, the therapeutic dosage range is from about 0.1 to about 100 mCi for $YCl_3$, from about 1 to about 500 mCi for $^{111}$In—Cl, and from about 1 to about 100 mCi for F-18 FDG. The upper limits on the therapeutic windows can be derived from the systemic toxicity profiles of the known toxicity profiles of the same radiopharmaceuticals upon systemic administration. A curie (Ci) is the basic unit used to describe the intensity of radioactivity in a sample of material. The curie is equal to 37 billion ($3.7 \times 10^{10}$) disintegrations per second, which is approximately the activity of 1 gram of radium. A curie is also a quantity of any radionuclide that decays at a rate of 37 billion disintegrations per second. In preferred embodiments, the radiation absorbed by a subject from the radiopharmaceutical administered as disclosed herein is from about 1 to 500 Gray (Gy), more preferably about 2, 3, 4, 5, 10, 15, 20, 25, 30, 35, 40, 45, 50, 55, 60, 65, 70, 75, 80, 85, 90, 95, 100, 125, 150, 175, 200, 250, 300, 350, 400, or 450 Gy. In other preferred embodiments, dose penetration will be determined by the 10% isodose range (distance from the edge of the lesion where the radiation absorbed dose is 10% that inside the lesion). Preferably the range will be, for example, for the targeted abnormal tissue (e.g., lesion) itself and preferably about a 0.5 to 2 cm margin beyond the targeted abnormal tissue, more preferably about a 1 to 1.5 cm margin beyond the targeted abnormal tissue.

In accordance with the present disclosure, "an effective amount" of the radiopharmaceuticals disclosed herein is defined as an amount sufficient to ablate or kill abnormal cells or tissue. An effective amount of the radiopharmaceutical may be administered in one or more injections. The effective amount of a given radiopharmaceuticals will vary according to factors such as the degree of susceptibility of the subject to the radiopharmaceutical, the age, sex, and weight of the subject, idiosyncratic responses of the subject, and the dosimetry of the particular radiopharmaceutical. Optimization of such factors is well within the level of skill in the art. For example, radiation dosimetry profiles may be generated and correlated with in vivo efficacy. Organ distribution of the radiopharmaceutical in animals can also be extrapolated to generate human radiation dosimetry profiles. Three components are also available to help one of skill in the art calculate an estimation of absorbed doses to tissues surrounding the site of administration of the radiopharmaceutical: 1) the energy deposited in the surrounding tissues is determined using radiation transport analysis (MCNP manual, Monte Carlo N-Particle Transport Code System. RSIC 1994, incorporated herein by reference); 2) the geometry of the activity distribution (source region) is determined using MR image data; and 3) the total number of radioactive transitions that occur in the region are determined using data from a scintigram. Both beta and gamma emissions are preferably evaluated. The total radiation absorbed doses may be derived for the abnormal tissue, for example a tumor, as well as surrounding tissues. Volumetric data measured from MRI may also be used to derive the S-values of the tumors using voxel-based simulation (Yoriyaz et al., *J Nucl Med* 42:662-29, 2001, incorporated herein by reference) to calculate the radiation absorbed doses of the sites of administration and surrounding tissues.

In the literature there are simplistic schemes of dosimetry to estimate radiation doses delivered to an organ or tissues from a point-source or nodules of defined size (e.g., MIRDose 3.1, Stabin M., (1996) *J Nucl. Med.* 37:538-546). The inventor has also developed a means for calculating radiation dosimetry profiles by using Monte Carlo simulations of spheres and shells models filled with 19 different radionuclides, including radionuclides used in the present disclosure (FIG. 1). Preliminary results using these simulations have been presented in the abstracts Wong et al., (2001) *J Nucl. Med.* 42:243 P and Wong et al., (2002) *J. Nucl. Med.* 43:5, 90P, each incorporated herein by reference. These simulations not only allow the calculation of conventional dosimetry values inside the spheres/shells, but also allow for the calculation of depth dosimetry (radiation does across different distances from the source). Depth dosimetry can be used to establish the efficacy of treatment and safety margins at distances up to 15 cm away from the radiation source. Therefore, these simulations can be adapted by one of skill in the art to calculate the dosimetry of a radiopharmaceutical by accurately measuring the volume and radioactivity distribution of the radiopharmaceutical in a subject using MRI/CT and/or Gamma cameras over the course of treatment, as well as depth dosimetry to better establish efficacy and safety margins.

The radiopharmaceuticals disclosed herein can be used for abnormal tissue or cell ablation by interstitial/locoregional injection, for example, by intratumoral injection, intracavitary, intrathecal injection, interstitial injection, intramuscular injection, or intralesional injection. For example, targeted ablation of abnormal tissues or cells is achieved when these radiopharmaceuticals are delivered through intratumoral or interstitial injection. In other preferred embodiments, the radiopharmaceuticals are applied topically to the skin, subcutaneously, or intradermally. The term "locoregional" primarily refers to sequestration of radionuclides from all of these routes of administration. The radiopharmaceutical may be administered by any of the above routes at a single location, or in several different locations in the same subject, for example, there may be multiple injection sites in a single tumor. If the radiopharmaceutical is administered to a subject in multiple locations, these administrations may occur at the same time, or over a period of time (e.g., fractionation) for effective treatment.

In preferred embodiments, the radiopharmaceuticals disclosed herein are used for locoregional radionuclide therapy of abnormal tissues or cells, for example neoplasms. As used herein, the term "neoplasm" refers to any malignant or benign neoplasm, as well as malignant or benign cancers, solid cancers, and tumors (including any carcinoma, sarcoma, or adenoma). A neoplasm is abnormal tissue that grows by cellular proliferation more rapidly than normal, and can continue to grow after the stimuli that initiated the new growth has ceased. A neoplasm may also have partial or complete lack of structural organization and functional coordination with normal tissue. As used herein, the term "solid cancers" includes but is not limited to the following: bladder tumor, bone tumor, brain tumor, cervical tumor, liver tumor, mammary tumor, ovarian tumor, pituitary tumor, pancreatic tumor, pituitary tumor, prostate tumor, testicular tumor, thyroid tumor, uterine tumor, Wilms' tumor, meninges, adenocarcinoma, adenoma, astrocytoma, Burkitt lymphoma, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, melanoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, lymphoma, liposarcoma cell, medulloblastoma, myeloma, plasmacytoma, neuroblastoma, neuroglioma, osteogenic sarcoma, retinoblastoma, rhabdomyosarcoma, sarcoma, thymoma, and the like.

In other preferred embodiments, the radiopharmaceuticals disclosed herein are used for radiosynoviorthesis (Gynter Mödder, Radiosynoviorthesis: Involvement of Nuclear Medicine in Rheumatology and Orthopaedics, 31-54 (Warlich Druck und Verlagsges. Germany, 1995) (2001), incorporated herein by reference). The term "radiosynoviorthesis" as used herein refers to the restoration of the synovia by the radiopharmaceutical. Inflammatory diseases such as arthritis are often caused by an inflammatory response of unknown origin in the synovium, or lining, of an afflicted joint. Local application of the radiopharmaceutical is done to influence the synovial process favorably, and as an alternative to surgical synovectomy. Radiosynoviorthesis indications include but are not limited to local therapy of the synovitis; osteoarthritis; rheumatoid diseases such as rheumatoid arthritis, psoriatic arthritis, and Bechterew's disease; villonodular synovitis; haemarthrosis in the haemophiliac; activated arthroses such as knee arthrosis, Baker's cyst, hip arthrosis, condition after total knee replacement, finger polyarthrosis, and rhizarthrosis; dialysis-arthropathies/amyloidosis; and tenosynovitis. In preferred embodiments, the radiopharmaceutical is injected or punctured into a subject's anesthetized joint (e.g., knee or hip), for the treatment of inflamed synovial tissue. If the initial radiosynoviorthesis treatment is not satisfactory for the subject, for example there is insufficient reduction of pain, local hyperthermia, and/or swelling, the radiosynoviorthesis can be repeated as often as needed. Preferably, however, a second radiosynoviorthesis treatment is performed at least six months after the first treatment.

In preferred embodiments, the radiopharmaceutical used for radiosynoviorthesis emits alpha or beta (including positrons) particle energy sufficient to penetrate and ablate the synovial tissue, but not so great as to damage underlying articular cartilage or overlying skin. The radiopharmaceutical preferably produces necrosis of abnormal cells in the synovia, as well as a decrease in inflammatory cell proliferation. Preferably, the radiopharmaceutical is biodegradable to prevent induction of granulomatous tissue. In other embodiments, the smaller the joint, the shorter the radiation penetrating distance of the radiopharmaceutical used. The effective dose range for radiosynoviorthesis with radiopharmaceuticals depends on many parameters, all of which are familiar to those of skill in the art, including but not limited to the radionuclide used, the injected amount, the size of the joint space, synovial thickness, synovial structure, distribution of the radiopharmaceutical in the joint, condition of the joint fluid, and inflammatory activity of the synovitis.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLE 1

To determine whether $YCl_3$ is able to suppress tumor growth, the activity of the radionuclide was compared to $^{111}$In chloride ($^{111}$In—Cl) and Thallium-201 chloride ($^{201}$Tl-Ci), as well as $^{90}$Y iron radiopharmaceutical macroaggregates (YIMA), which have previously been shown to suppress tumor growth (U.S. Ser. No. 10/724,027, incorporated herein by reference). The radionuclides $YCl_3$, $^{111}$In—Cl, and $^{201}$Tl—Cl were obtained from a local supplier of radioisotopes, Iso-Tex Diagnostics (Friendswood, Tex.). $YCl_3$ obtained from the supplier was in an acidic preparation with a pH of 2-3, and was subsequently diluted in saline to a final pH of about 4-6 before injection. Initial activities of $^{111}$In—Cl and $YCl_3$ were about 200-500 mCi/ml, and dilution were made with preservative-free saline. YIMA was prepared by co-precipitation, as set forth in U.S. Ser. No. 10/724,027. Briefly, 500 μl of $FeCl_3$ (1 mg Fe/ml) was added to 30 μl of $^{90}$Y chloride (20-40 μCi/30 μl), and either 30 μl of NaOH (1.0 N) or 10 μl of $NH_4OH$ (20.0%) was added to the solution to reach a pH of about 7.0 to 9.0. Co-precipitated YIMA radiopharmaceutical macroaggregates were then separated from remaining soluble radionuclides by centrifuging the reactions from 1500 RPM to 3000 RPM×5 minutes, and filtered using a Millipore Nylone (size: 0.45 μm, diameter: 13 mm) to isolate the radiopharmaceutical macroaggregates.

The rat model of in vivo tumor growth was generated as follows. On day zero, 100,000 rat mammary cancer 13762F tumor cells were implanted in a volume of 0.15 ml into the right thigh muscle of Fischer 344 female rats weighing approximately 160 grams. On day 10 the rats were injected intratumorally again in the right thigh with the following: (1) 0.6 mCi $^{111}$In—Cl; (2) 0.6 mCi $^{201}$Tl-Ci; (3) 100 μCi $YCl_3$; (4) 200 μCi $YCl_3$; (5) 500 μCi $YCl_3$; (6) 1 mCi $YCl_3$; (7) 1 mCi YIMA; and (8) Phosphate Buffered Saline (PBS). The $YCl_3$, $^{111}$In—Cl, and $^{201}$Tl-Ci were administered to the rats in 0.1-0.2 ml saline (pH 4.5-6). YIMA was injected in a volume of 0.2 ml on days 3-7 after tumor implantation. Tumor sizes and body weights of the rats were monitored regularly (5 times a week) for several weeks, or until the tumors grew beyond 2.5 cm, at which time the rats were euthanized.

Figure 2:
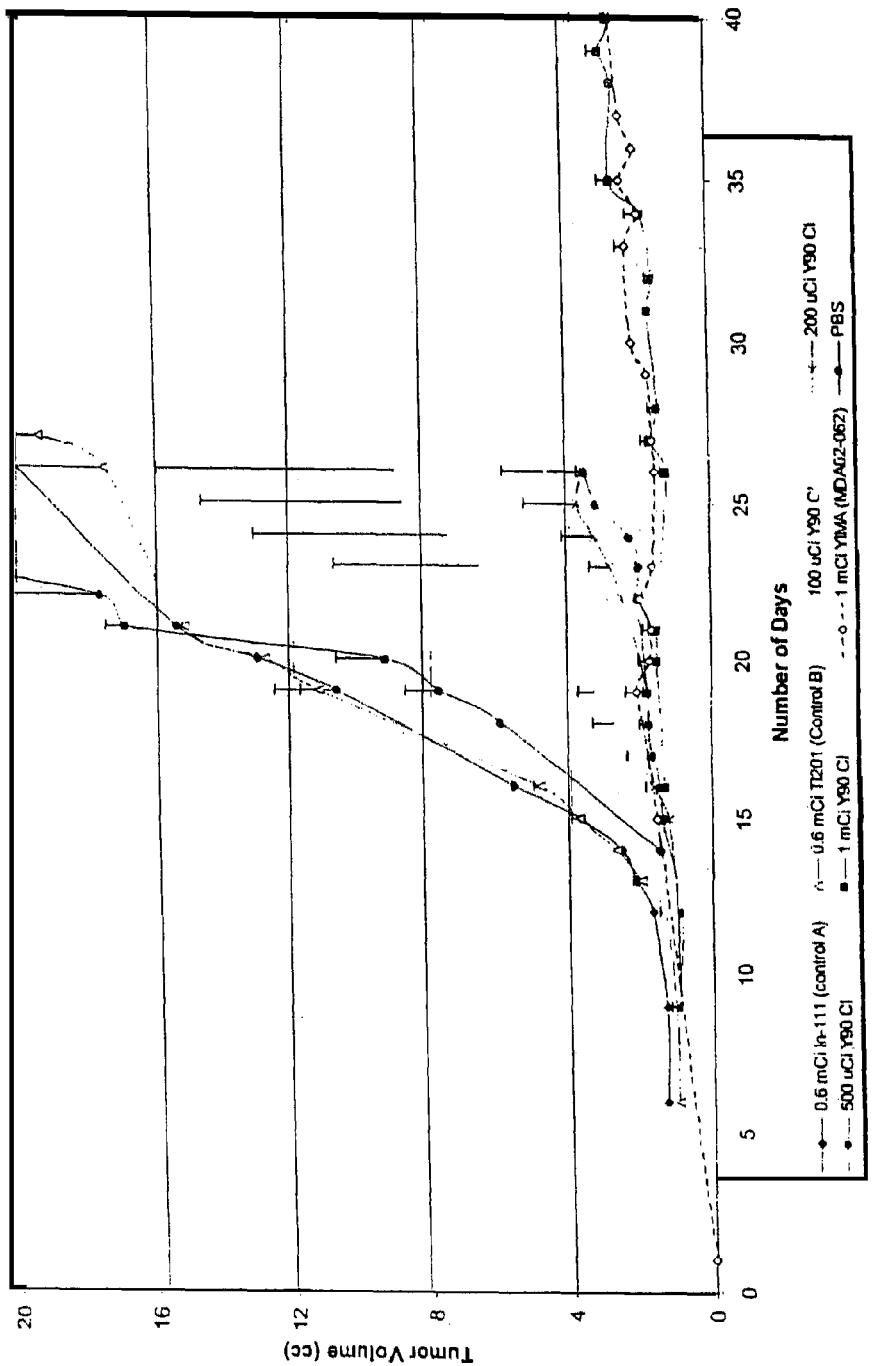
FIG. 2. Graph of in vivo rat tumor growth rates after treatment with the radiopharmaceutical Yttrium-90 chloride (YCl$_3$). On day zero, 100,000 rat mammary cancer 13762F tumor cells were implanted into the right thigh muscle of Fischer 344 female rats. On day 10, after the tumors became palpable, the rats were injected intratumorally with one of the following: (1) 0.6 mCi $^{111}$In—Cl; (2) 0.6 mCi $^{201}$Tl—Cl; (3) 100 μCi YCl$_3$; (4) 200 μCi YCl$_3$; (5) 500 μCi YCl$_3$; (6) 1 mCi YCl$_3$; (7) 1 mCi $^{90}$Y iron radiopharmaceutical macroaggregates (YIMA); and (8) Phosphate Buffered Saline (PBS). Tumor sizes were monitored regularly and the in vivo tumor growth rates over time are shown. Tumor growth was clearly suppressed in rats treated with at least 200 μCi of YCl$_3$, as well as rats treated with YIMA (a positive control). Tumor growth was not suppressed in rats treated with 0.6 mCi $^{111}$In—Cl.

The results of the experiments demonstrated that $YCl_3$ is able to suppress tumor growth in vivo in rats, in a dose-response relationship. As shown in FIG. 2, tumor development was not reduced in rats treated with PBS, 0.6 mCi $^{111}$In—Cl, or 0.6 mCi $^{201}$Tl—Cl. Tumor growth in rats treated with 100 μCi $YCl_3$ was also not significantly suppressed. When the dose of $YCl_3$ was increased to 200 μCi, 500 μCi, or 1 mCi, however, tumor development was significantly suppressed. The level of suppression was comparable to the suppression shown by 1 mCi YIMA, the positive control. These experiments demonstrate that $YCl_3$ may be used for nonspecific ablation when placed in proximity with abnormal tissue. Although some mortality was observed during locoregional ablation experiments with rats using $YCl_3$, it occurred sporadically at high dose equivalents for humans (e.g., 350 mCi/70 Kg). While this mortality level suggests a ceiling for human applications, local tumor suppression effects of $YCl_3$ have been consistently observed with doses as low as 0.2 mCi, indicating a large therapeutic window for the administration of $YCl_3$.

Figure 3:
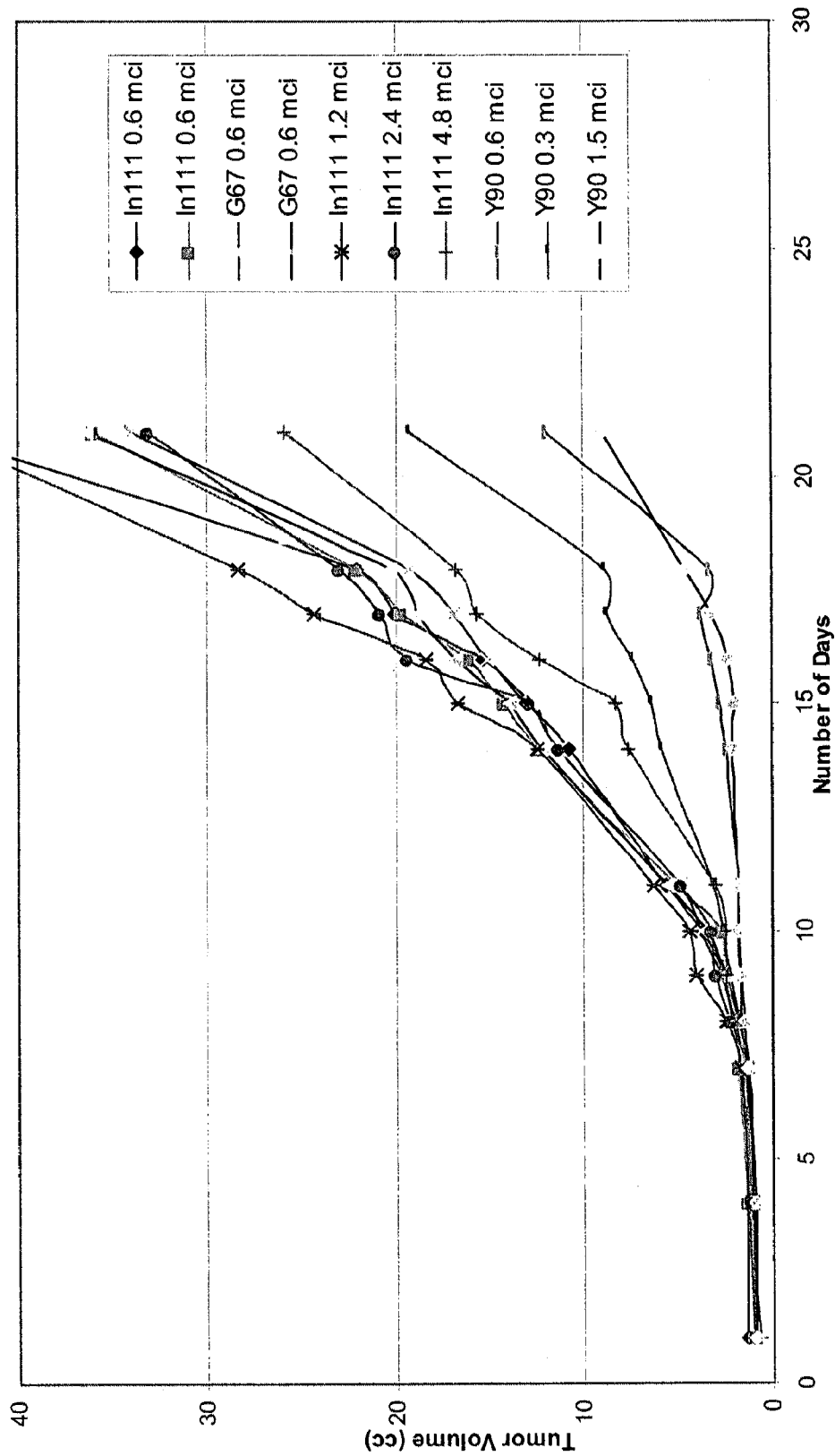
FIG. 3. Graph of in vivo rat tumor growth rates after treatment with the following radiopharmaceuticals administered in 0.2-0.3 ml of saline: 0.6 mCi $^{111}$In—Cl; 1.2 mCi $^{111}$In—Cl; 2.4 mCi $^{111}$In—Cl; 4.8 mCi $^{111}$In—Cl; 0.6 mCi $^{67}$Ga; 0.6 mCi YCl$_3$; 0.3 mCi YCl$_3$; and 1.5 mCi YCl$_3$. YCl$_3$ appeared to be the only radiopharmaceutical that significantly suppressed tumor growth.
Figure 4:
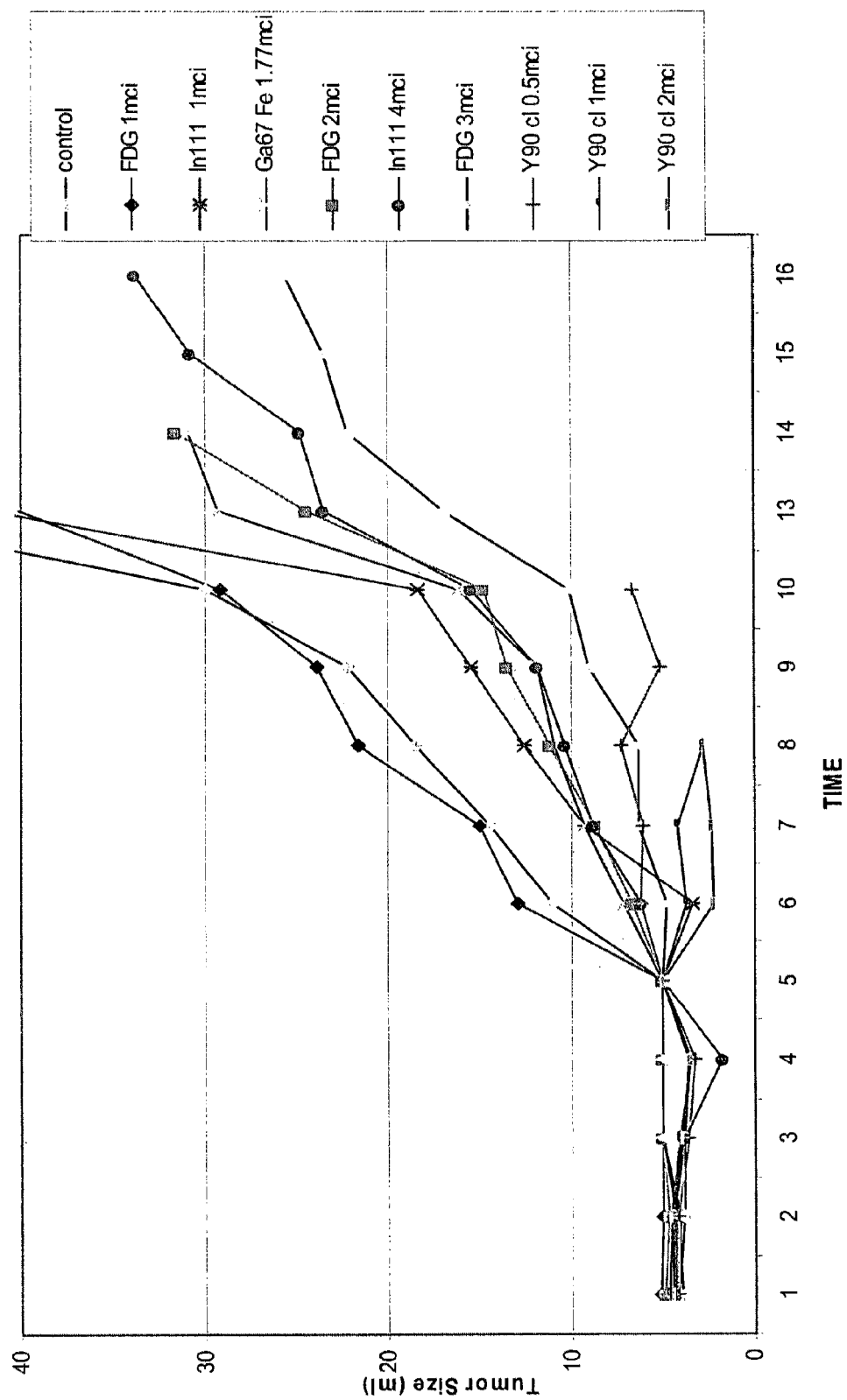
FIG. 4. Graph of in vivo rat tumor growth rates after treatment with the following radiopharmaceuticals administered in 0.5 ml of saline: 1.0 mCi $^{111}$In—Cl; 4.0 mCi $^{111}$In—Cl; 1.0 mCi FDG; 2.0 mCi FDG; 3.0 mCi FDG; 1.77 mCi $^{67}$Ga—Fe; 0.5 mCi YCl$_3$; 1.0 mCi YCl$_3$; and 2.0 mCi YCl$_3$. YCl$_3$ appeared to be the only radiopharmaceutical that significantly suppressed tumor growth.
Figure 5:
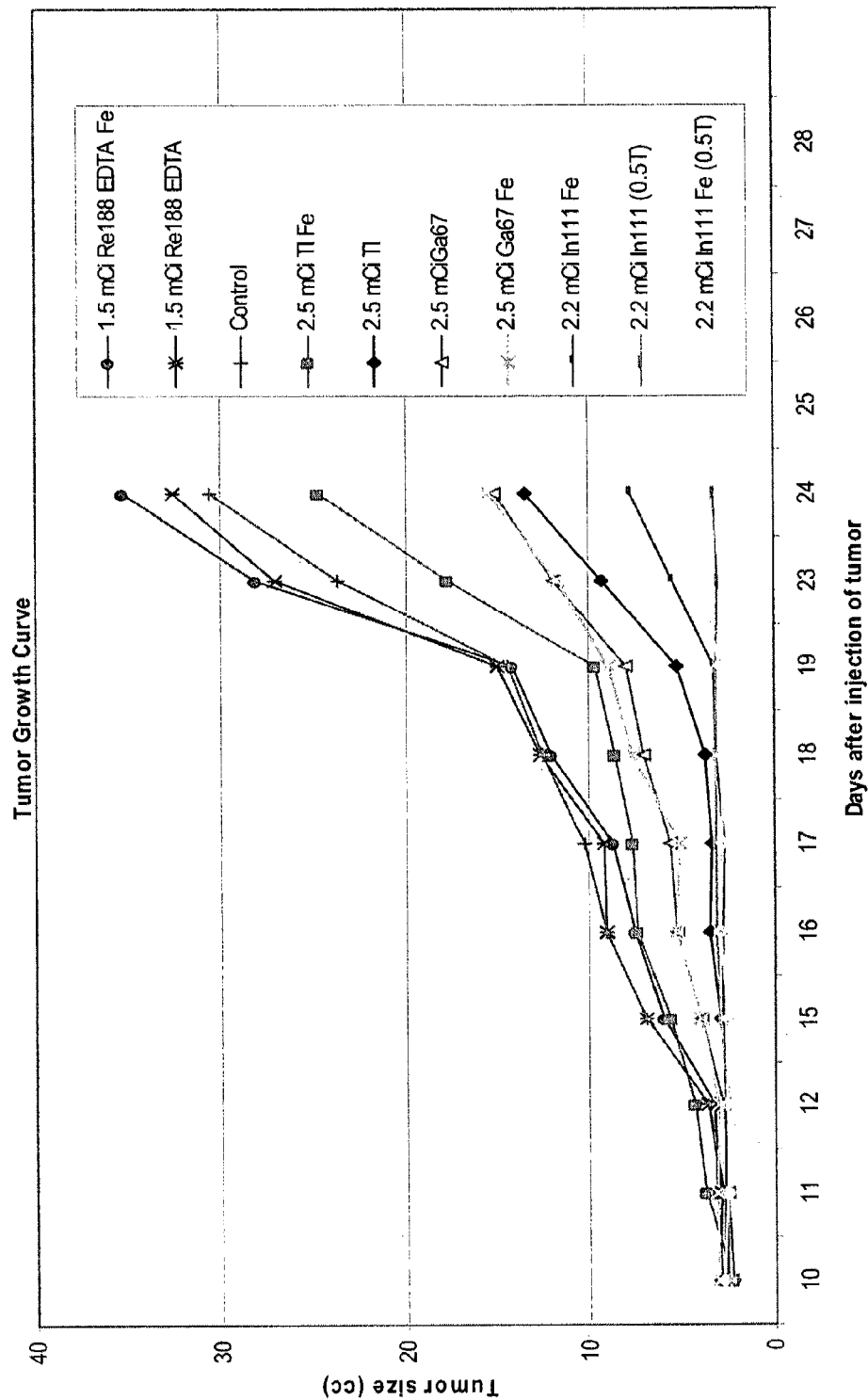
FIG. 5. Graph of in vivo rat tumor growth rates after treatment with the following radiopharmaceuticals administered in 1.0 ml of saline: 2.2 mCi $^{111}$In—Cl; 2.2 mCi $^{111}$In—Cl—Fe; 2.5 mCi $^{67}$Ga; 2.5 mCi $^{67}$Ga—Fe; 2.5 mCi $^{201}$Tl; 2.5 mCi $^{201}$Tl—Fe; 1.5 mCi $^{188}$Re EDTA; and 1.5 mCi $^{188}$Re-EDTA-Fe. Surprisingly, $^{111}$In—Cl exhibited strong tumor suppression in the increased injectate volume.

After the results of the above experiments indicated that $^{111}$In—Cl did not suppress tumor development, the experiments were repeated, but the volume of injectate used to deliver $^{111}$In—Cl was increased to determine if a greater volume would increase the tumor suppression ability of $^{111}$In—Cl. Surprisingly, a dramatic increase in tumor suppression by $^{111}$In—Cl was observed when the injection volume was increased from 0.2-0.3 ml (FIG. 3) and 0.5 ml (FIG. 4) to 1.0 ml (FIG. 5). Thus, $^{111}$In—Cl is also able to suppress tumor growth in vivo in rats, provided the $_{111}$In—Cl is administered in a sufficiently high volume.

EXAMPLE 2

Figure 6:
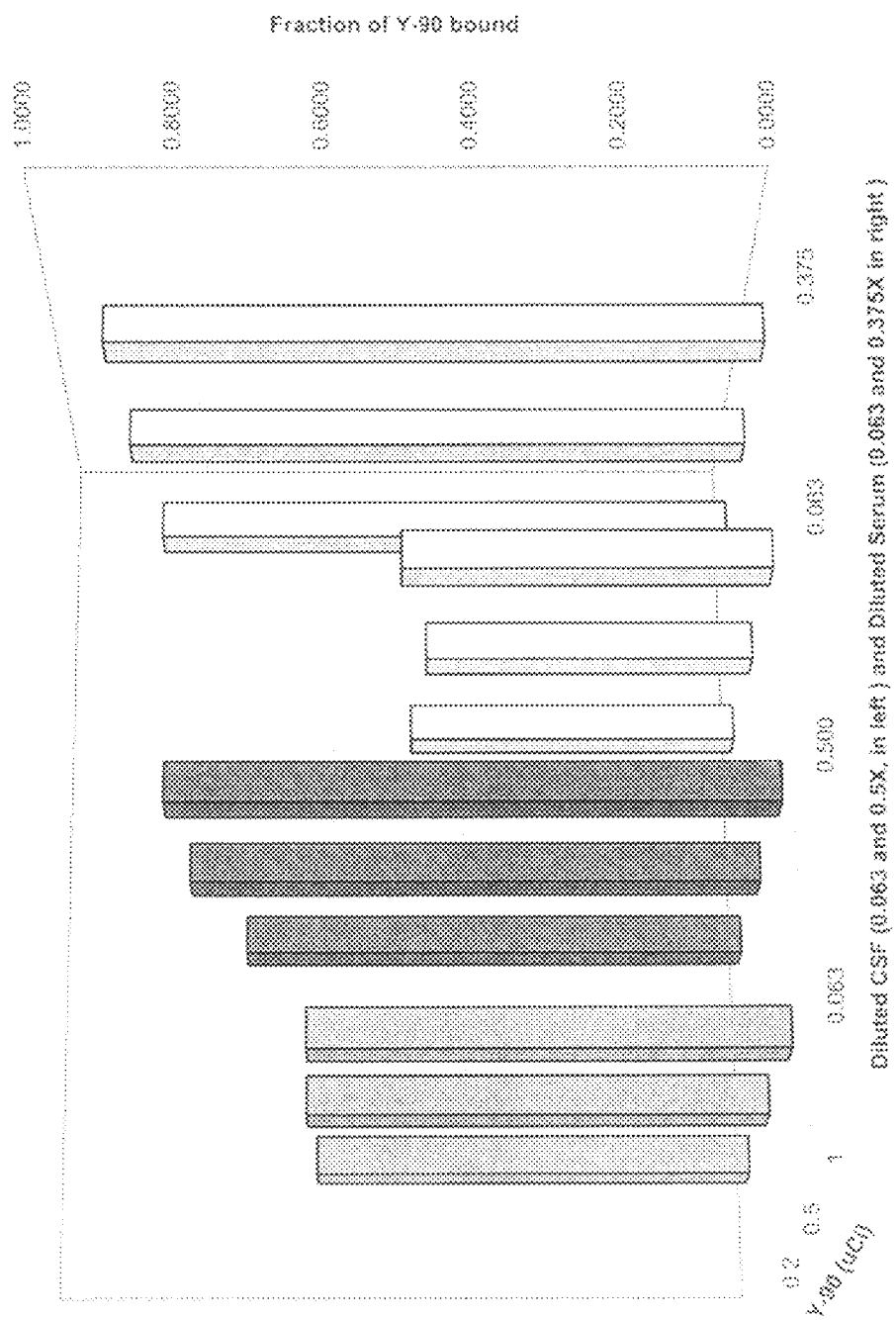
FIG. 6. Demonstration of YCl$_3$ binding to cerebrospinal fluid and serum proteins. Varying amounts of YCl$_3$ (0.2, 0.5, or 1 μCi) were added to diluted CSF (1:0.063 or 1:0.5) or diluted serum protein (1:0.063 or 1:0.375), and free $^{90}$Y was separated from protein bound $^{90}$Y using Millipore Centrifree filters. As shown, YCl$_3$ binds avidly to CSF and serum protein within the physiologic range at all concentrations tested.
Figure 7:
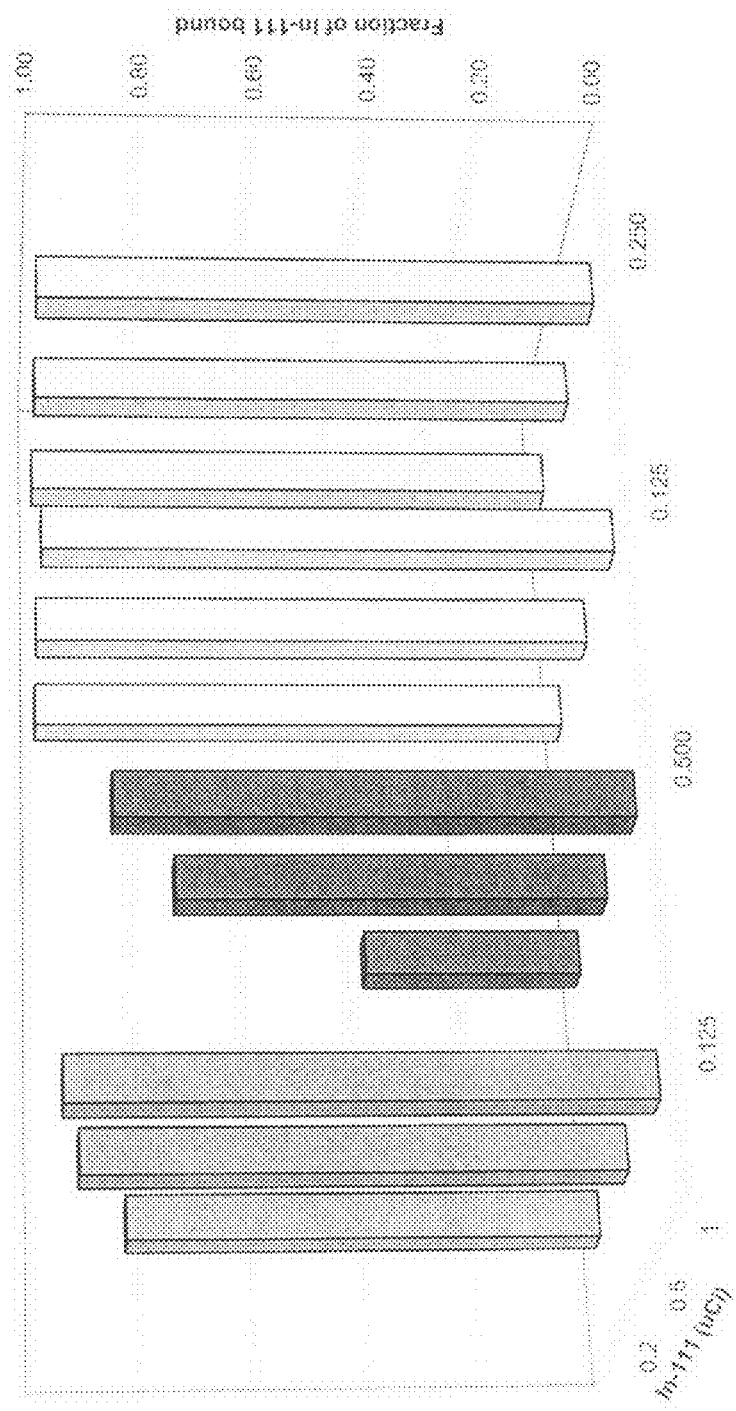
FIG. 7. Demonstration of $^{111}$In—Cl binding to cerebrospinal fluid and serum proteins. Varying 0.2, 0.5, or 1 μCi of $^{111}$In—Cl was added to diluted CSF (0.125 or 0.5) or diluted serum protein (0.125 or 0.25), and free $^{111}$In was separated from protein bound $^{111}$In using Millipore Centrifree filters. As shown, $^{111}$In—Cl binds avidly to CSF and serum protein within the physiologic range at all concentrations tested.

To test the hypothesis that local sequestration of $^{111}$In—Cl is due to protein binding, both $^{111}$In—Cl and $YCl_3$ were tested for binding to CSF and serum proteins. Serum proteins were obtained from residual baseline serum and CSF proteins were obtained from patients participating in other research protocols who had consented to blood sampling. To determine the level of $^{111}$In—Cl protein binding, 0.2, 0.5, or 1 μCi of $^{111}$In—Cl was added to diluted CSF (0.125 or 0.5) or diluted serum protein (0.125 and 0.25) and incubated for 20 minutes. To determine the level of $YCl_3$ protein binding, 0.2, 0.5, or 1 μCi of $YCl_3$ was added to diluted CSF (0.063 or 0.5) or diluted serum protein (0.063 and 0.375), and incubated for 20 minutes. After incubation, free radiopharmaceuticals were separated from protein bound $^{111}$In—Cl or $YCl_3$ using Amicon Centrifree Micropartition filters in a single centrifugation step at 3000 g for 15 minutes according to manufacturer's instructions (Amicon, Beverly, Mass.). The percent binding of $YCl_3$ or $^{111}$In—Cl to the CSF or serum protein was then calculated. As shown in FIG. 6 and FIG. 7 respectively, both $YCl_3$ and $^{111}$In—Cl bind avidly to CSF and serum protein within the physiologic range (a dilution factor between 0.2 and 0.6) at all concentrations tested. At room temperature, both $YCl_3$ and $^{111}$In—Cl have greater than 95% binding to serum proteins.

EXAMPLE 3

Figure 8:
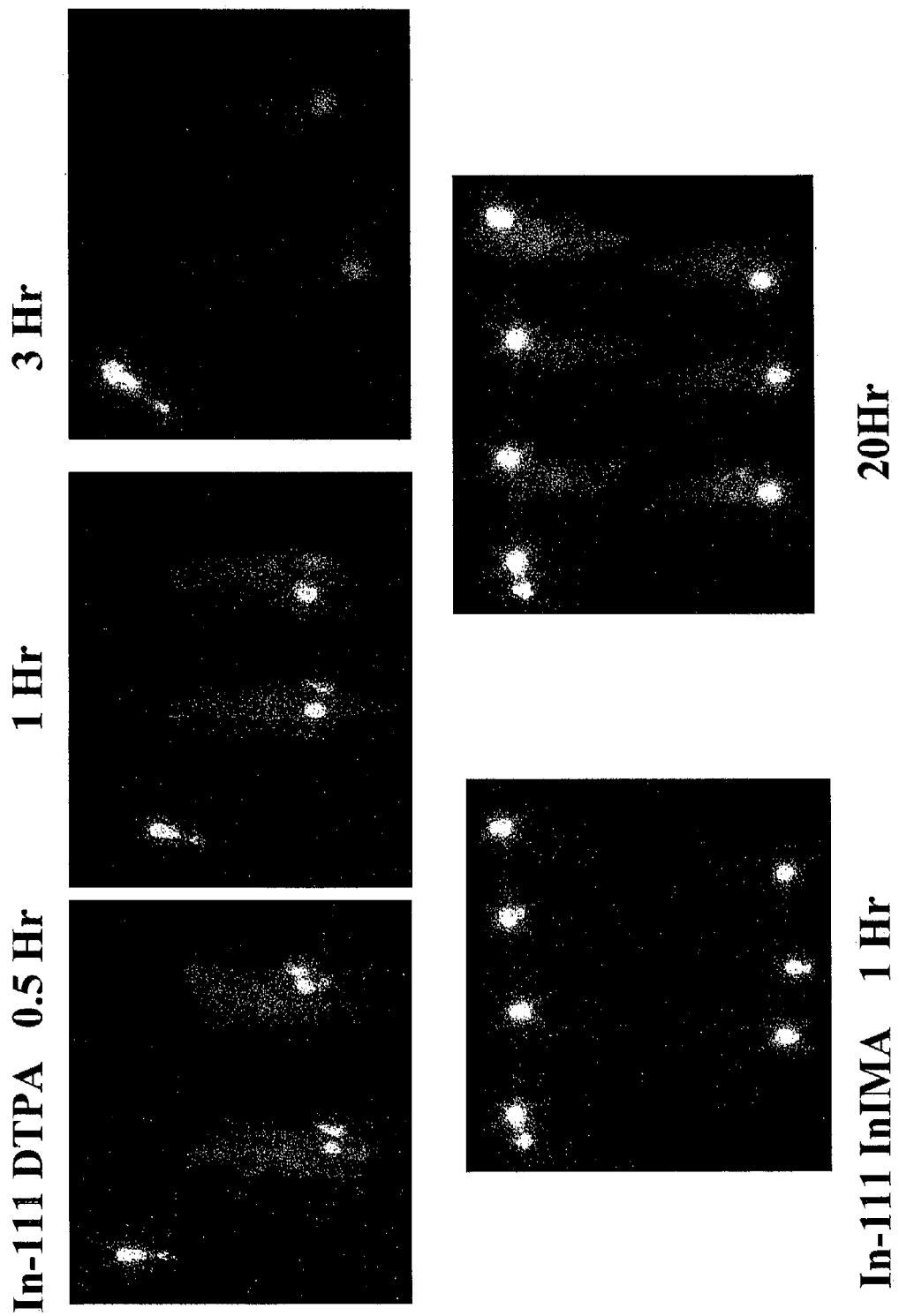
FIG. 8. Intramuscular injection of $^{111}$In-DTPA and Indium-111-Iron Macroaggregate ($^{111}$In-IMA). $^{111}$In-DTPA and $^{111}$In-IMA were each injected intramuscularly (IM) into the thigh muscle of 2 and 5 Fischer 344 rats respectively. Serial scintigrams demonstrate that $^{111}$In-DTPA was rapidly cleared in the rats, whereas $^{111}$In-IMA was still present in the injection area (84%) after 70 hours.
Figure 9:
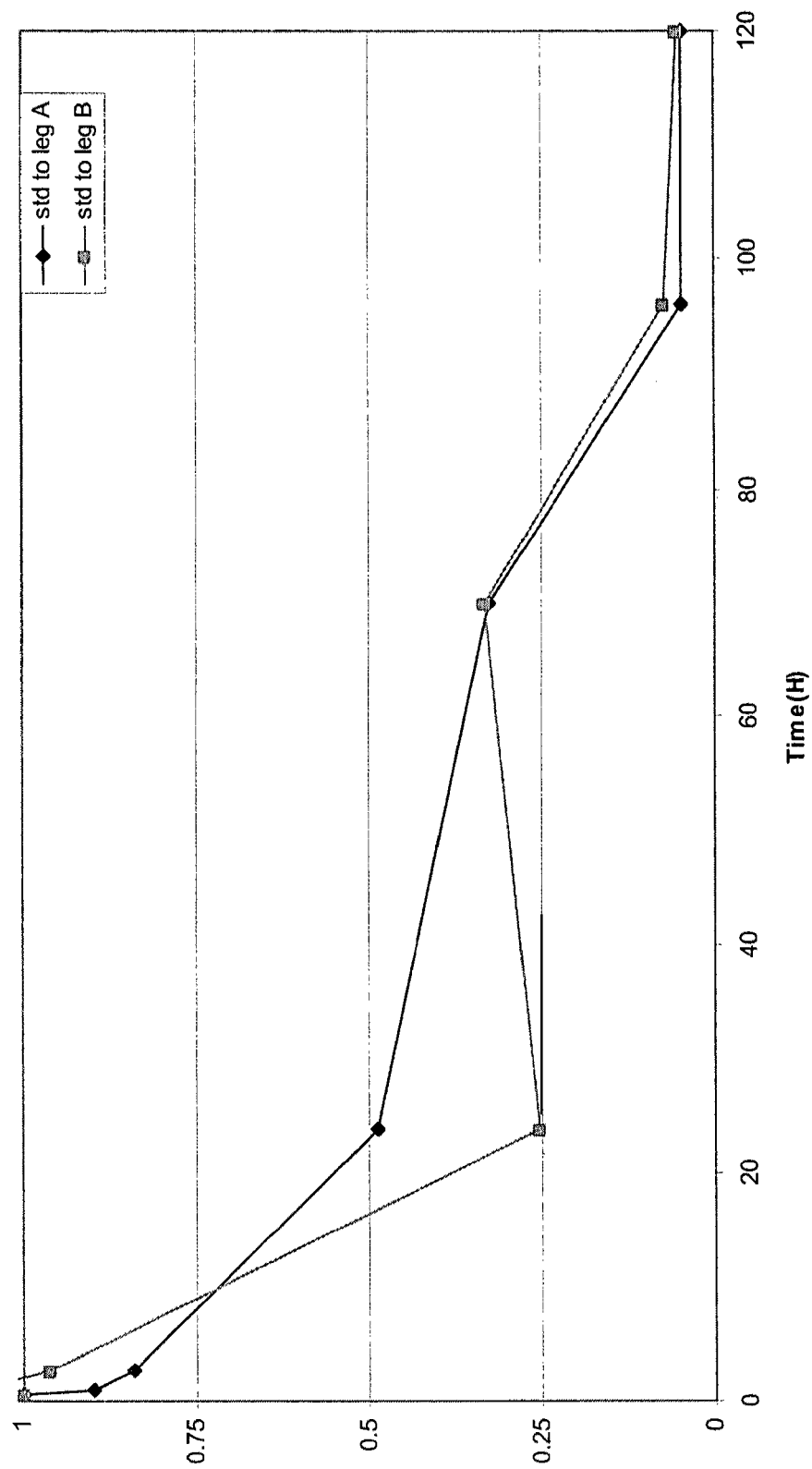
FIG. 9. Graph of in vivo local sequestration in rats of $^{111}$In—Cl after intramuscular injection of an acidic solution of $^{111}$In—Cl (pH 3.0) and a basic solution of $^{111}$In—Cl (pH 8.0). The pH of the IM injected $^{111}$In—Cl does not appear to dramatically affect the local sequestration of $^{111}$In—Cl.

To further study the localization of unsealed radiopharmaceuticals after injection, in vivo imaging studies were carried out comparing $^{111}$In DTPA (In-DTPA) (negative control) and Indium-111-Iron Macroaggregate ($^{111}$In-IMA) (positive control) to $^{111}$In—Cl. $^{111}$In emits gamma rays that can be detected using a gamma camera. $^{111}$In-IMA was generated according to methods disclosed in U.S. Ser. No. 10/724,027, incorporated herein by reference. Each radiopharmaceutical was administered by intramuscular injection into the thigh muscle of Fischer rats which weighed approximately 200 grams. Two different doses of $^{111}$In—Cl were administered to the rats, 0.4 and 0.8 mCi in 0.2 ml saline. Distribution of the $^{111}$In—Cl was determined through serial scintigrams. When In-DTPA was administered to rats, the rats demonstrated rapid clearance of the In-DTPA after only 3 hours (FIG. 8). In comparison, when $^{111}$In-IMA was administered to rats, consistent retention (84%) of the $^{111}$In-IMA was found 70 hours after administration (FIG. 8). Persistent intramuscular localization of $^{111}$In—Cl was also found in rats for both dose levels of $^{111}$In—Cl, with over 50% of the injected $^{111}$In—Cl remaining in the injection site after three days. These results indicate local sequestration of $^{111}$In—Cl after locoregional injection. As shown in FIG. 9, varying the pH of the IM injected $^{111}$In—Cl does not appear to dramatically affect the local sequestration of $^{111}$In—Cl.

EXAMPLE 4

To investigate whether the addition of free iron to radionuclides would increase the locoregional retention of various radionuclides, admixtures of $^{67}$Ga-citrate, YCl$_3$, or $^{111}$In—Cl, were prepared with FeCl3.6H2O at 1-5 mg Fe/ml. Each radionuclide combination/admixture was administered either by intramuscular (IM) injection into the thigh muscle of the left leg (0.1-1.0 mCi) or by intratumoral (IT) injection into a tumor in the right leg (0.4-5.0 mCi) of Fischer rats. Distribution of the radionuclide was determined through serial scintigrams. Whole body images were acquired with a Siemens M-CAM camera using respective photo peaks of Ga-67, Tl-201 (for Y-90), or In-111, and 15-20% windows in photo energy. The typical imaging time was 0.5 to 5 minutes. A respective standard was present in the field of view (0.1-0.5 mCi), and used for image quantification by comparing images with the standard and normalizing the initial injection time as 100%. The Fe content in each combination/admixture was 1 mg in the total injectate. Increase in the retention time was noted with $^{67}$Ga-citrate, $^{67}$Ga—Cl, YCl$_3$, and $^{111}$In—Cl.

Figure 10:
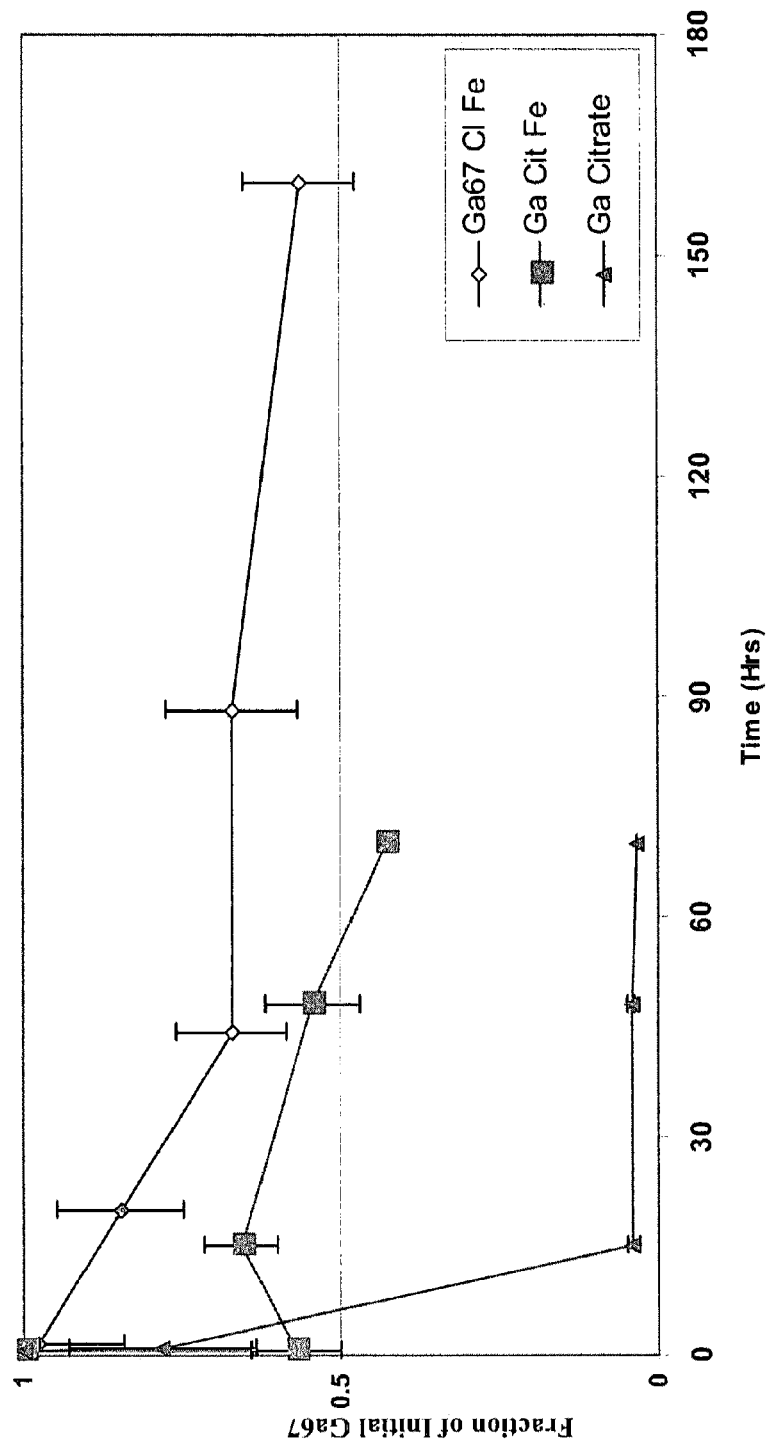
FIG. 10. Graph of in vivo local sequestration in rats after intramuscular injection of $^{67}$Ga—Cl/Fe, $^{67}$Ga-citrate/Fe, and $^{67}$Ga citrate. The presence of free iron in the injectate greatly increased $^{67}$Ga retention.
Figure 11:
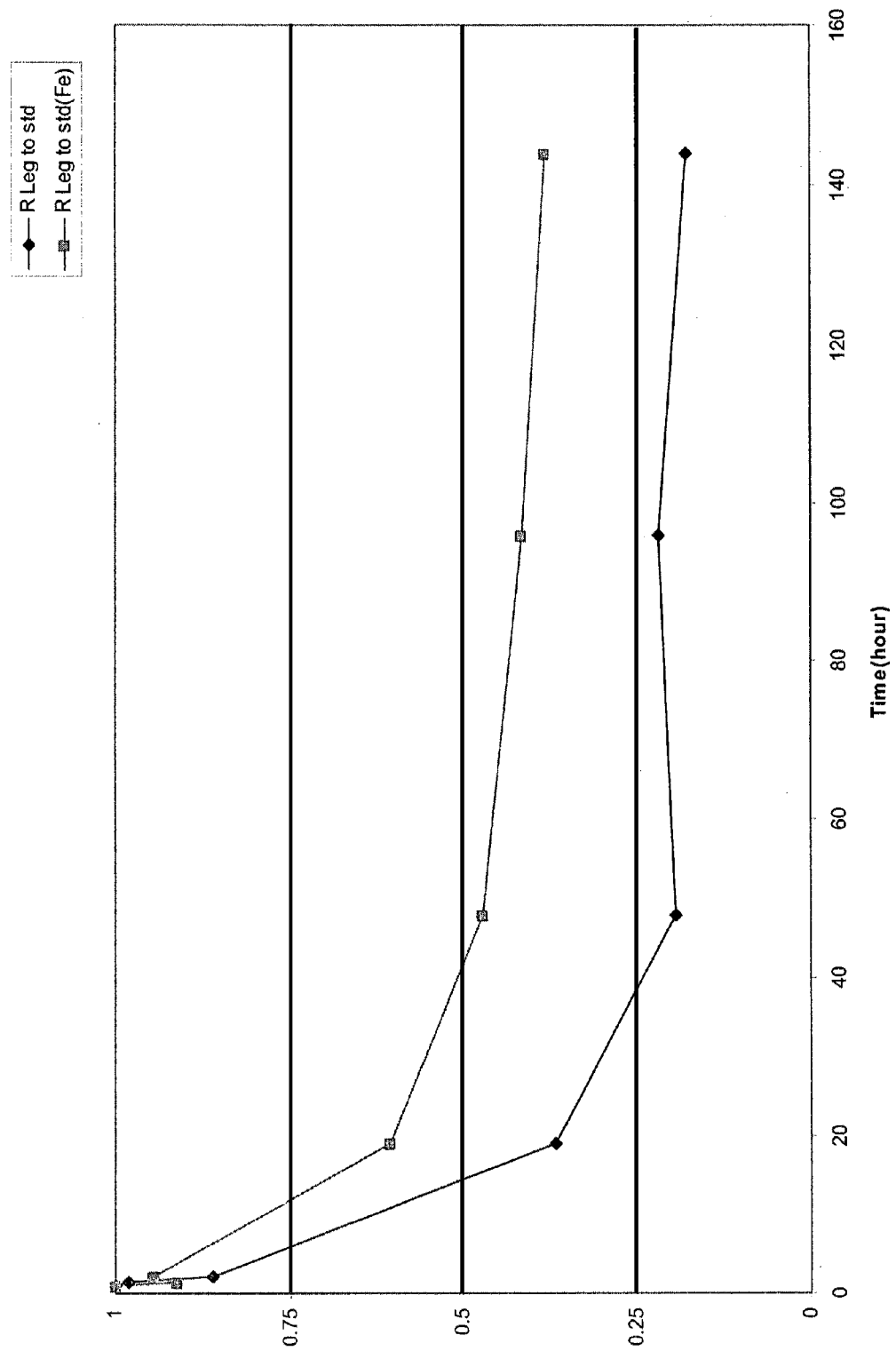
FIG. 11. Graph of in vivo local sequestration in rats after intratumoral injection of $^{67}$Ga-citrate/Fe and $^{67}$Ga citrate. The presence of free iron in the injectate greatly increased $^{67}$Ga retention.

FIG. 10 shows $^{67}$Ga retention after intramuscular injection of $^{67}$Ga—Cl/Fe admixture, $^{67}$Ga-citrate/Fe admixture, and $^{67}$Ga citrate. While $^{67}$Ga citrate is retained in the injection site for a comparatively short time, the presence of free iron with $^{67}$Ga citrate and $^{67}$Ga—Cl greatly increases $^{67}$Ga retention. A similar result was obtained after intratumoral injection of $^{67}$Ga-citrate/Fe admixture and $^{67}$Ga citrate (FIG. 11). Again, the presence of free iron in the injectate increased $^{67}$Ga retention.

Figure 12:
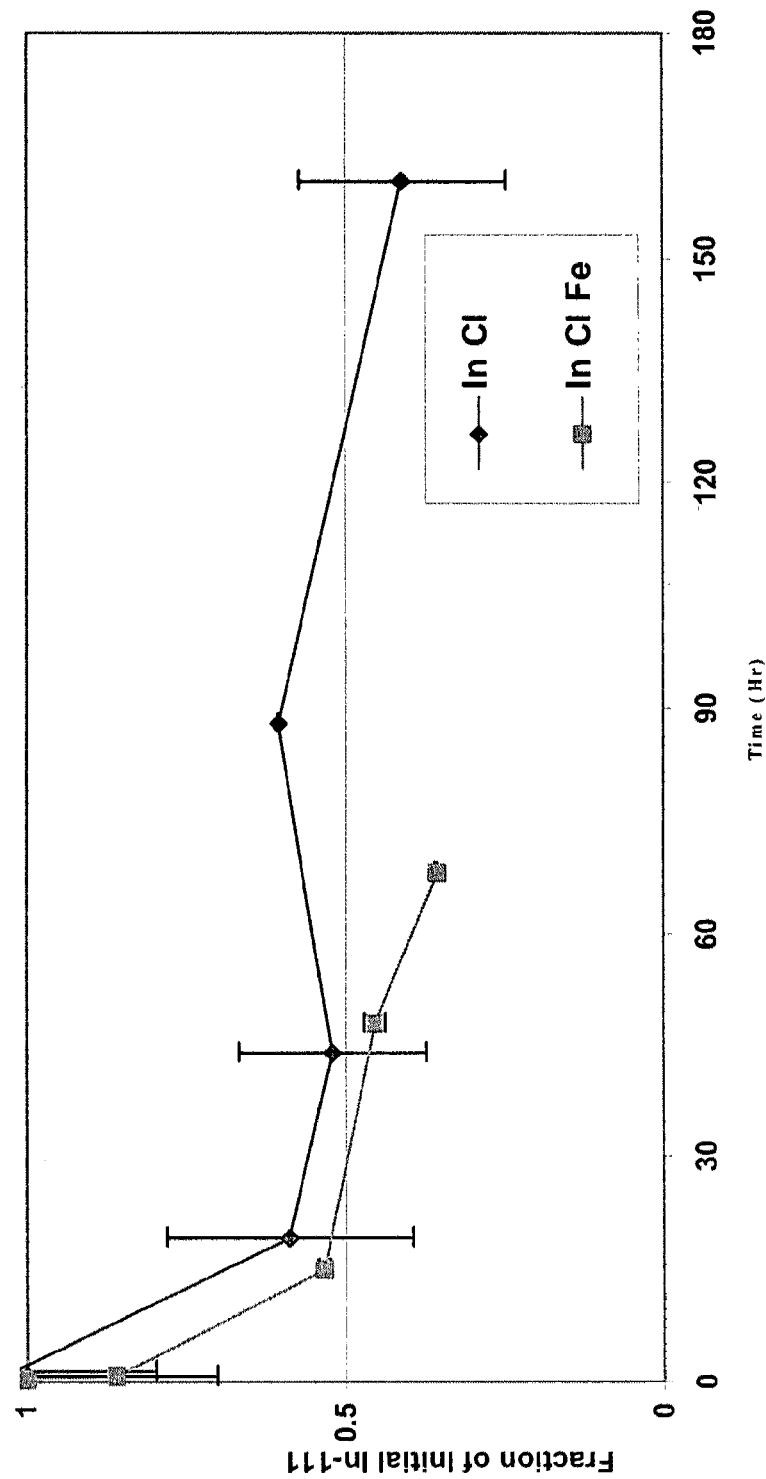
FIG. 12. Graph of in vivo local sequestration in rats after intramuscular injection of $^{111}$In—Cl—Fe and $^{111}$In—Cl. The presence of free iron in the injectate did not appear to increase $^{111}$In—Cl retention.
Figure 13:
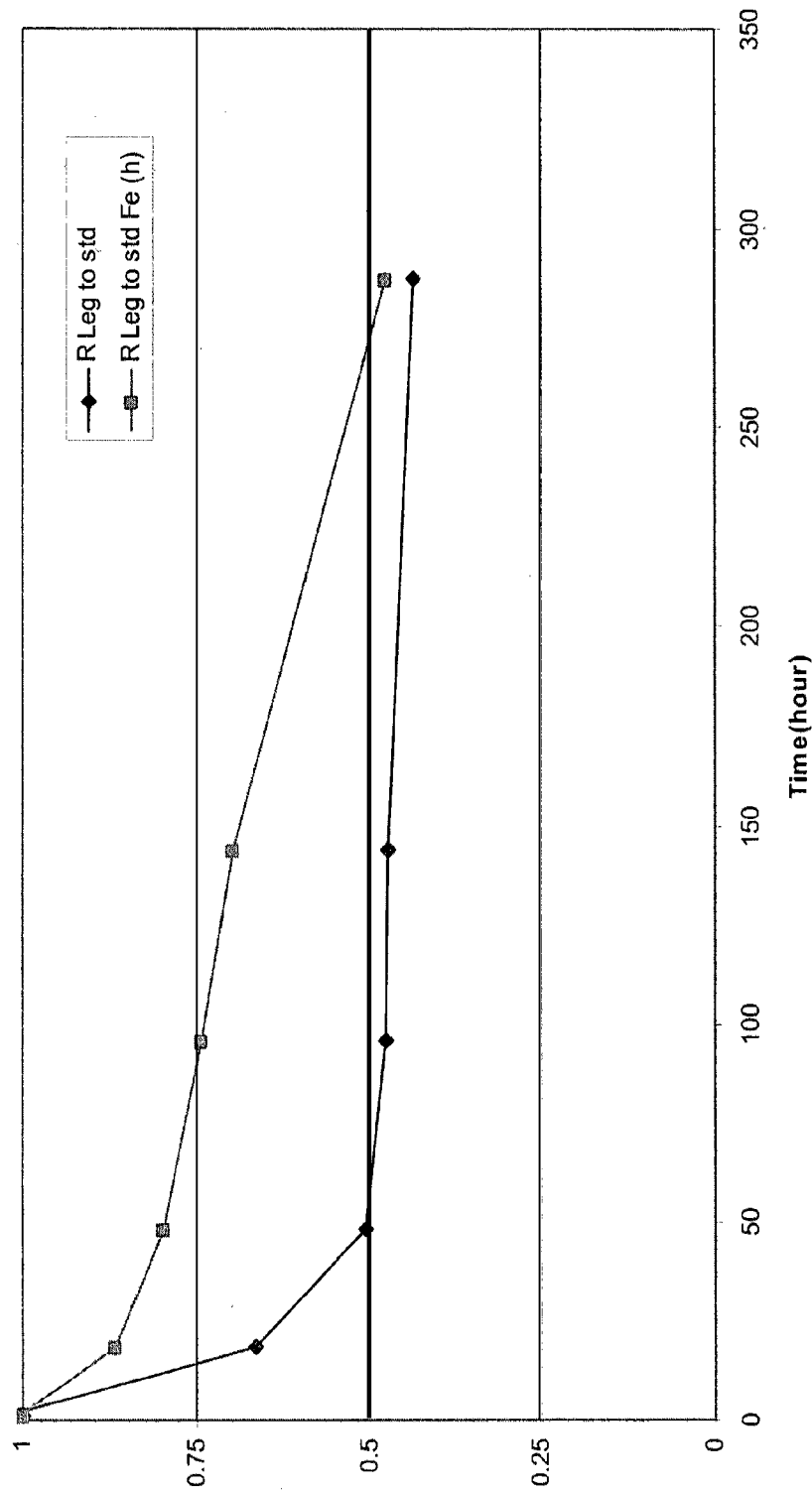
FIG. 13. Graph of in vivo local sequestration in rats after intratumoral injection of $^{111}$In—Cl—Fe and $^{111}$In—Cl. The presence of free iron in the injectate did appear to increase $^{111}$In—Cl retention.
Figure 14:
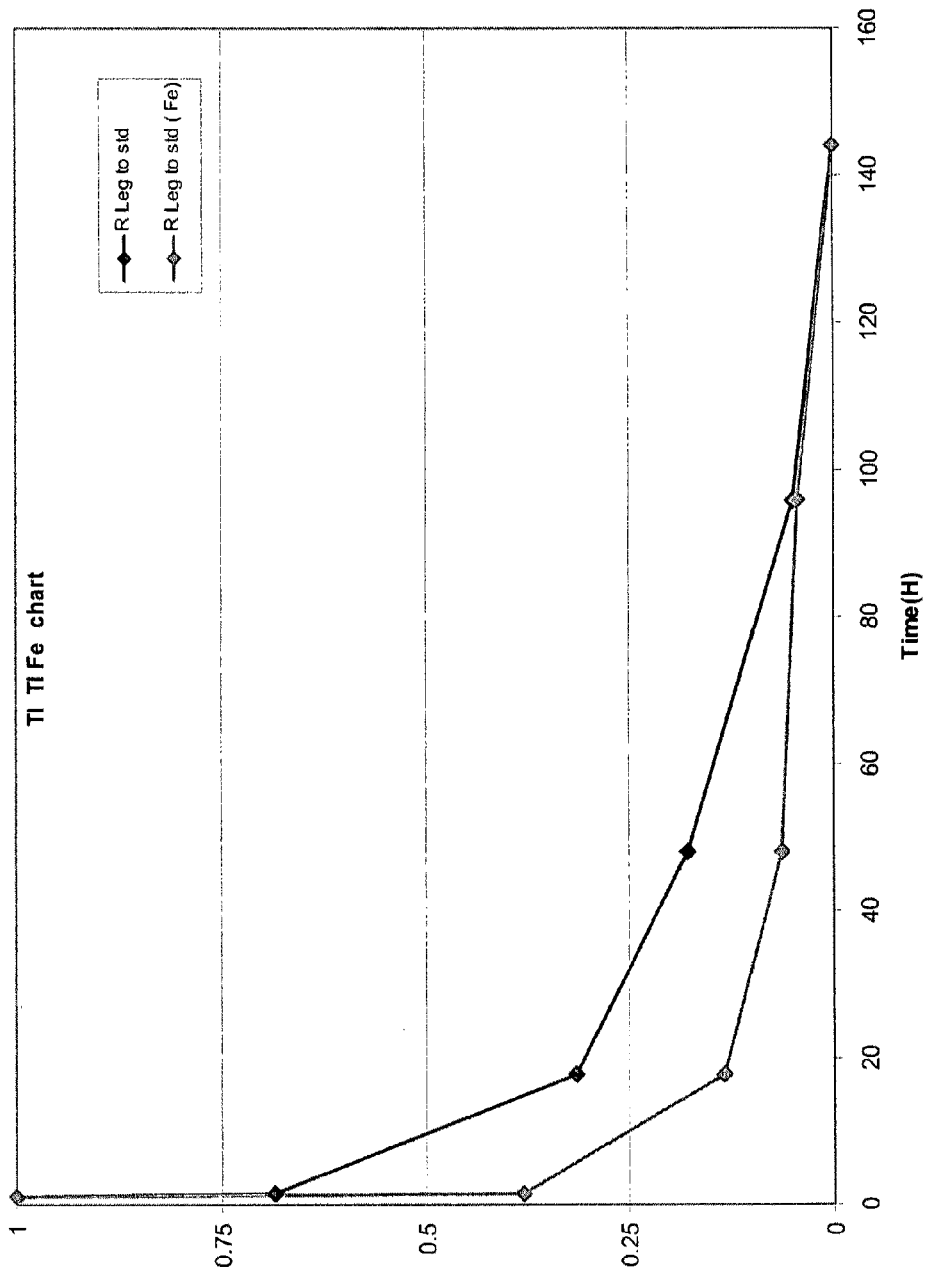
FIG. 14. Graph of in vivo local sequestration in rats after intratumoral injection of $^{201}$Tl—Cl—Fe and $^{201}$Tl—Cl. The presence of free iron in the injectate did not appear to increase $^{201}$Tl—Cl retention.

As demonstrated above in Example 3, $^{111}$In—Cl is locally sequestered after locoregional injection. Interestingly, adding free iron to $^{111}$In—Cl does not appear to dramatically affect the local sequestration of $^{111}$In—Cl when injected intramuscularly (FIG. 12), but does appear to increase local sequestration of $^{111}$In—Cl when injected intratumorally (FIG. 13). In contrast, the addition of free iron to $^{201}$Tl—Cl did not dramatically slow down clearance of $^{201}$Tl from an intratumoral injection site (FIG. 14).

Figure 15:
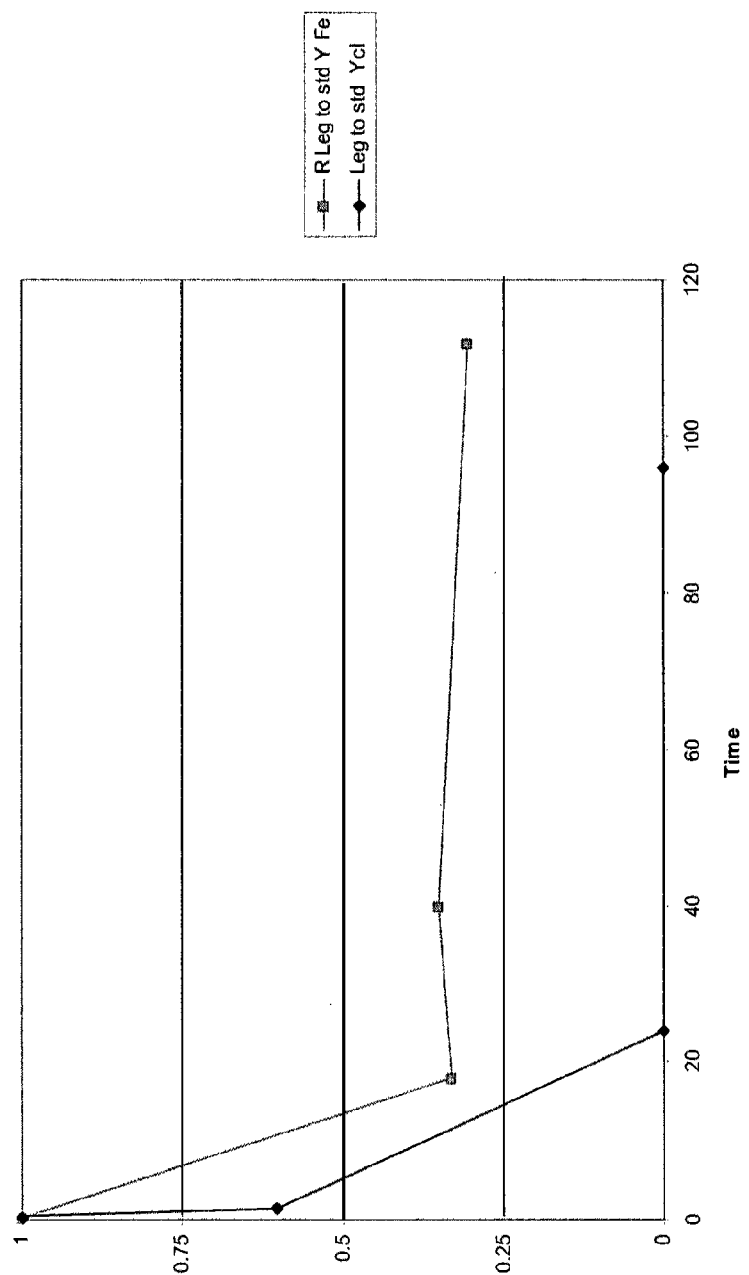
FIG. 15. Graph of in vivo local sequestration in rats after intramuscular injection of YCl$_3$/Fe and YCl$_3$. The presence of free iron in the injectate greatly increased $^{90}$Y retention.
Figure 16:
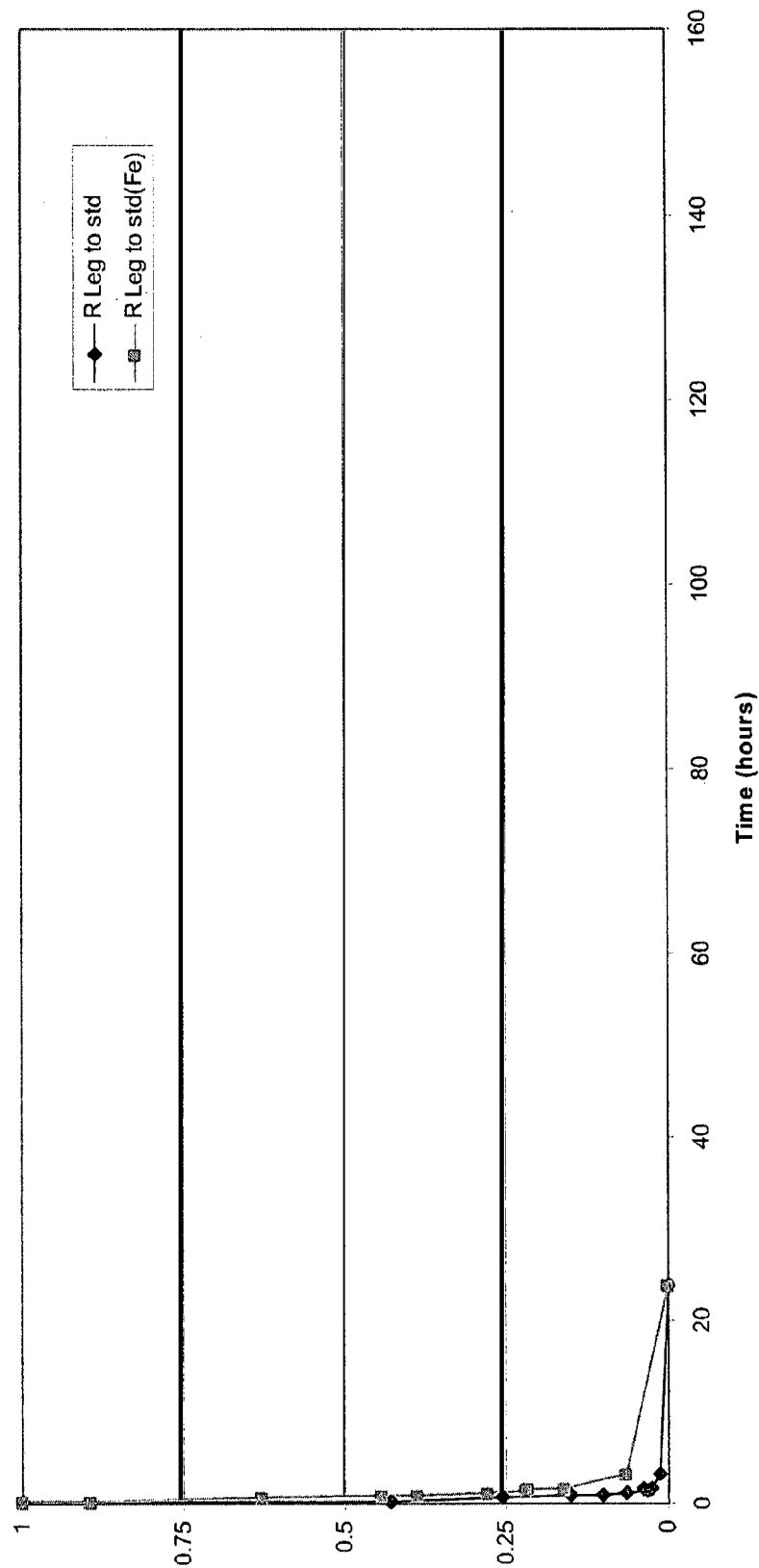
FIG. 16. Graph of in vivo local sequestration in rats after intratumoral injection of $^{188}$Re perrhenate/Fe and $^{188}$Re perrhenate. $^{188}$Re perrhenate was rapidly cleared from the injection site, and the presence of free iron in the injectate did not appear to increase $^{188}$Re perrhenate retention.
Figure 17:
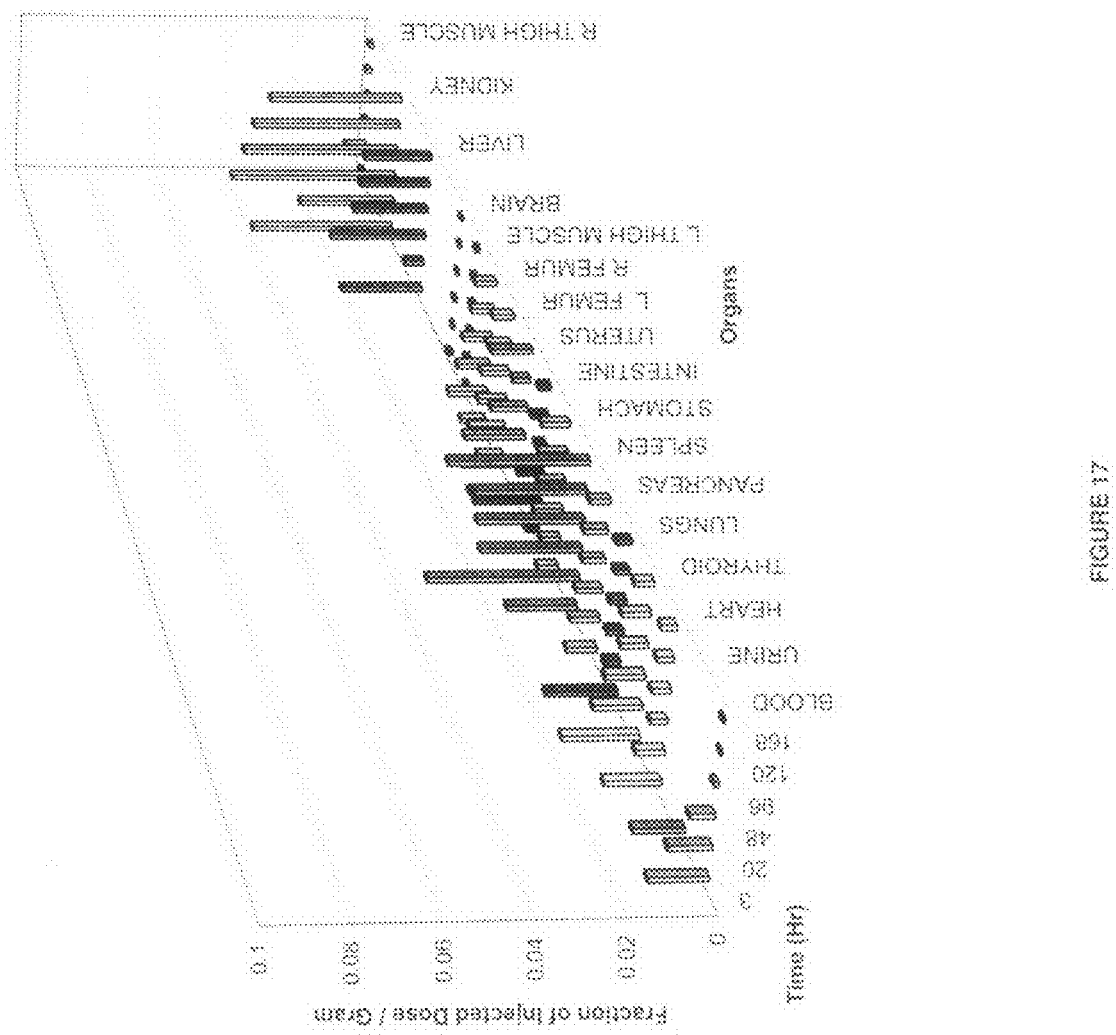
FIG. 17. Biodistribution of intravenously injected YCl$_3$ in Fischer 344 rats demonstrates that the spleen, liver, and kidney take up the highest doses of systemically administered YCl$_3$.

The presence of free iron did increase the retention of YCl$_3$. FIG. 15 compares $^{90}$Y retention after intramuscular injection of YCl$_3$ and YCl$_3$/Fe admixture. These results indicate that in contrast to $^{111}$In—Cl, YCl$_3$ is rapidly cleared over approximately 20 hours after IM injection in rats, indicating that YCl$_3$ is not locally sequestered. The presence of free iron with YCl$_3$, however, increases $^{90}$Y retention to greater than 100 hours. Even though YCl$_3$ is not locally sequestered, it surprisingly is able to suppress tumor growth in vivo in rats, as shown in Example 1. This result is surprising because one of skill in the art would have expected YCl$_3$ to diffuse so quickly from the injection site that it would be unable to suppress tumor growth. For example, $^{128}$Re perrhenate is rapidly cleared from the injection site after intratumoral injection (FIG. 16), suggesting that $^{128}$Re perrhenate would be unable to suppress tumor growth in vivo. The addition of free iron to $^{128}$Re perrhenate did not slow down the clearance of $^{128}$Re perrhenate from the injection site at all. This suggestion is confirmed in FIG. 5, which shows that $^{128}$Re perrhenate EDTA was unable to suppress tumor growth (with or without the addition of free iron).

Thus, the addition of free iron to certain radionuclides, namely $^{67}$Ga, $^{111}$In, and $^{90}$Y, markedly prolonged the half-lives of these radionuclides in the injection site. Therefore, the addition of FeCl$_3$ appears to serve dual purposes: 1) to provide paramagnetic signals for detection of the distribution of the injectate; and 2) to provide an environment for the radionuclide for prolonged retention in the injection site.

EXAMPLE 5

Previous reports have found that the radiation toxicity of free Yttrium-90 ($^{90}$Y) is high (e.g., 15-18 cGy/mCi by ICRP-30) in red bone marrow, presumably because of high distribution of free $^{90}$Y to the skeleton. Reports estimate that as much as 50%-80% of intravenously injected $^{90}$Y was present in the bones four days after injection (Kutzner et al., (1981) *Nucl. Med.* 20:229-235). Another report studying the distribution of Yttrium-86 citrate from human PET studies derived lower doses (4-6 cGy/mCi) for $^{90}$Y (Herzog et al., (1996) *J. Nucl. Med.* 34:2222-2226). Previous reports also indicate that the liver and spleen are the primary target organs of intravenously injected YCl$_3$, and that the intravenously injected YCl$_3$ resulted in dose-dependent formation of colloidal material in blood plasma (Hirano et al., (1993) *Toxicol. Appl. Pharmacol.* 121:224-232). It has also been reported that intratracheal instillation of YCl$_3$ results in prolonged pulmonary retention of $^{90}$Y with a half-life of 169 days (Hirano et al., (1990) *Toxicol. Appl. Pharmacol.* 104:301-311).

To evaluate the radiation toxicity of YCl$_3$ after intravenous or intramuscular injection, parallel experiments were performed to evaluate the biodistribution and projected human radiation dosimetry of both $^{111}$In—Cl and YCl$_3$. The experiments used three female Fisher rats (140-160 grams) for each set of injections. Each rat was injected intravenously, or was injected intramuscularly in the right thigh, with 0.05 mCi of YCl$_3$ or $^{111}$In—Cl (with no carrier added) in 0.1 ml saline (pH 5-6). The effect of initial exposure of the radiopharmaceuticals to interstitial fluid was estimated by serum protein binding experiments using Millipore Centrifree filters as set forth in Example 2. Organs including the right and left femur, as well as the right and left thigh muscles, were harvested from each rat 7 days after injection. Human dosimetry for each radiopharmaceutical was constructed using established anthropomorphic models.

Figure 18:
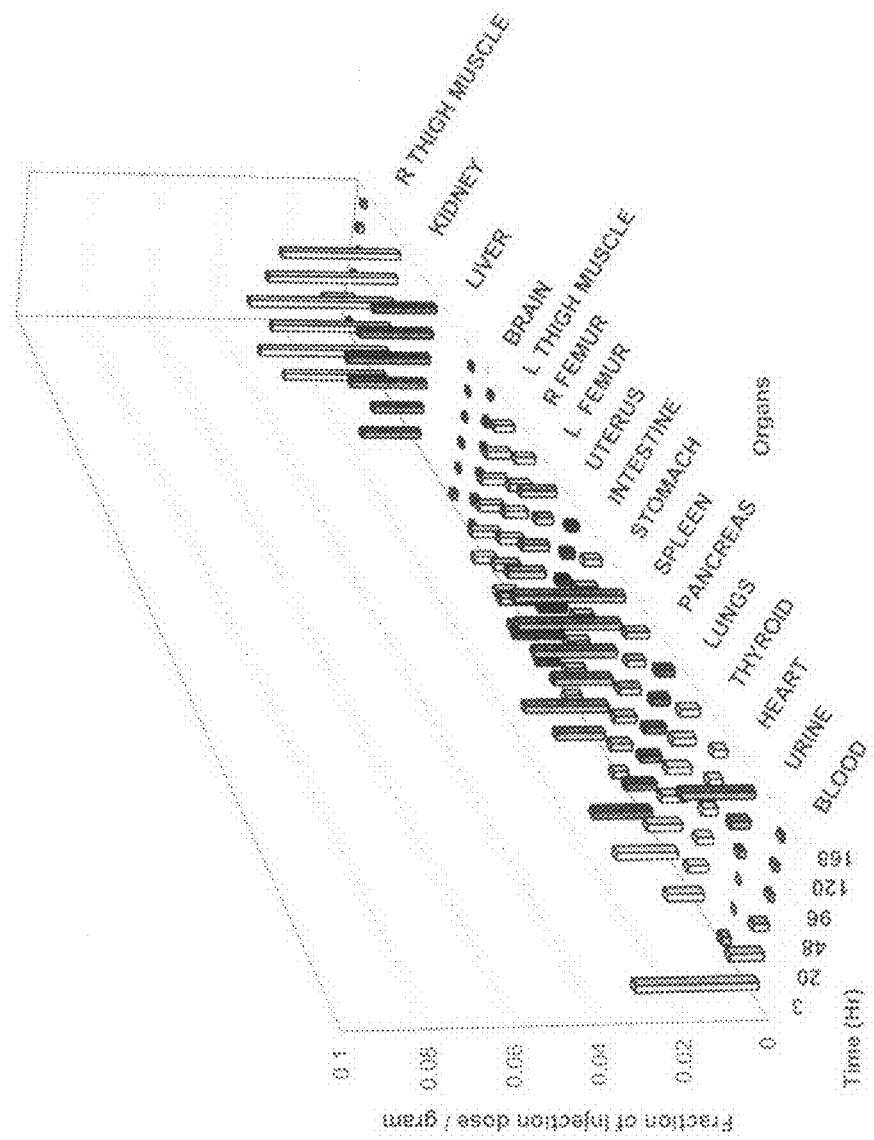
FIG. 18. Biodistribution of intravenously injected $^{111}$In—Cl in Fischer 344 rats demonstrates that the spleen, liver, and kidney take up the highest doses of systemically administered $^{111}$In—Cl.

Interestingly the biodistribution and radiation dosimetry profiles for both intravenous and intramuscular injection of YCl$_3$ and $^{111}$In—Cl were similar, and the serum binding measurements indicated greater than 99% initial binding of both YCl$_3$ and $^{111}$In—Cl to serum proteins. The estimated radiation dosimetry profile generated using the left femur (opposite to the injection site) indicated that the skeletal distribution of YCl$_3$ and $^{111}$In—Cl is about 16%, versus the published value of 50%. Measurement of radiation uptake in the right thigh muscle of intramuscularly injected YCl$_3$ and $^{111}$In—Cl were high, as expected, but surprisingly the measurements were also higher in the right femur than in the contralateral organ (6 times higher and decreasing over time to 3 times higher). The biodistribution data for intravenously injected $YCl_3$ and $^{111}$In—Cl, as shown in FIG. 18 and FIG. 19 respectively, demonstrate that $YCl_3$ and $^{111}$In—Cl are primarily taken up by the spleen, liver, and kidney, with kidney having the highest dose of any organ examined. The human dosimetry estimates based upon the mass estimation from the rat biodistribution and the values for red marrow were as follows: (1) 5.77 cGy/mCi for intravenous $YCl_3$; (2) 4.01 cGy/mCi for intravenous $^{111}$In—Cl; (3) 0.65 cGy/mCi for intramuscular $YCl_3$; and (4) 0.55 cGy/mCi for intramuscular $^{111}$In—Cl. The human dosimetry estimates for kidney, which had the highest doses of any organ, were as follows: (1) 13.1 cGy/mCi for intravenous $YCl_3$; (2) 10.4 cGy/mCi for intravenous $^{111}$In—Cl; (3) 1.47 cGy/mCi for intramuscular $YCl_3$; and (4) 1.13 cGy/mCi for intramuscular $^{111}$In—Cl. Thus, the human dosimetry estimates indicate that both $YCl_3$ and $^{111}$In—Cl, when administered intramuscularly, have acceptable radiation toxicity levels, and are attractive radiopharmaceuticals for locoregional administration.

The above experiments indicate that red marrow radiation doses after intravenous administration of free $^{90}$Y may be significantly lower than that reported in the literature. In addition, the red marrow radiation dose is significantly lower after intramuscular administration of $^{111}$In—Cl, which is consistent with the proposal that $^{111}$In—Cl binds the interstitium upon injection. These experiments, and others which may be performed by those of skill in the art, will provide further guidance for planning intralesional therapy using $YCl_3$, $^{111}$In—Cl, or a combination of the two radionuclides.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for the locoregional treatment of abnormal tissue, comprising administering a composition comprising an unsealed and non-colloidal radiopharmaceutical to a subject in the region of the abnormal tissue, wherein the radiopharmaceutical is locally sequestered after introduction into the abnormal tissue, and has an effective amount of radioactivity for locoregional ablation of cells in the abnormal tissue, wherein the radiopharmaceutical is selected from the group consisting of Indium-111 chloride ($^{111}$In—Cl), Yttrium-90 chloride ($^{90}YCl_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide ($Na^{131}I$), Holmium-166 DOTMP (166Ho-DOTMP), Samarium-153 EDTMP ($^{153}$Sm-EDTMP), F-18-2-deoxy-2-fluoro-D-glucose (F-18 FDG), iododeoxyuridine, meta-iodobenzylguanidine, iodocholesterol (NP59), and combinations thereof, wherein the abnormal tissue comprises a neoplasm, tumor, or synovial tissue, wherein the administering comprises intratumoral injection, intralesional injection, intramuscular injection, intracavitary injection, interstitial injection, or intrathecal injection, and wherein the administering comprises administering the composition directly to the abnormal tissue.

2. The method of claim 1, wherein the subject is human.

3. The method of claim 1, wherein the radiopharmaceutical is $^{111}$In—Cl, $^{90}YCl_3$, or F-18 FDG.

4. The method of claim 1, wherein the radiopharmaceutical is a combination of $^{111}$In—Cl and $^{90}YCl_3$.

5. The method of claim 1, wherein the radiopharmaceutical is a combination of F-18 FDG and 111 In—Cl.

6. The method of claim 1, wherein the radiopharmaceutical is a combination of F-18 FDG and 90$YCl_3$.

7. The method of claim 1, wherein the radiopharmaceutical emits beta radiation, gamma radiation, or positrons.

8. The method of claim 1, wherein the composition is administered in saline solution.

9. The method of claim 1 further comprising measuring the distribution of the radiopharmaceutical by a method selected from the group consisting of magnetic resonance imaging (MRI), Positron Emission Tomography (PET), Computed Tomography (CT) scanner, Single Photon Emission Computed Tomography (SPECT), ultrasonography, high resolution gamma scintigraphy, and any combination thereof.

10. The method of claim 1 further comprising measuring a radiosensitizer.

11. The method of claim 10, wherein the radiosensitizer is 2-deoxy-D-glucose.

12. The method of claim 1 further comprising administering Rhodamine-123.

13. The method of claim 1 further comprising administering $FeCl_3$ or hydrated $FeCl_3$.

14. The method of claim 1 further comprising administering a non-radioactive imaging agent.

15. The method of claim 14, wherein the non-radioactive imaging agent is I-127 NaI, $FeCl_3$, hydrated $FeCl_3$, Ferrindex, Gadolinium-chloride, or Gadolinium-DTPA.

16. The method of claim 14, wherein the volume distribution of the radiopharmaceutical is estimated by measuring the distribution of the non-radioactive imaging agent.

17. The method of claim 16 further comprising measuring the distribution of the non-radioactive imaging agent by a method selected from the group consisting of magnetic resonance imaging (MRI), Positron Emission Tomography (PET), Computed Tomography (CT) scanner, Single Photon Emission Computed Tomography (SPECT), ultrasonography, high resolution gamma scintigraphy, and any combination thereof.

18. The method of claim 1, wherein the radiopharmaceutical is administered to the subject in a large injection volume that covers depths with about a 0.5 cm to 2 cm margin beyond the abnormal tissue.

19. The method of claim 18, wherein the large injection volume covers depths with about a 1.0 cm to 1.5 cm margin beyond the abnormal tissue.

20. The method of claim 19, wherein the radiopharmaceutical is $^{111}$In—Cl.

21. The method of claim 1 further comprising administering epinephrine.

22. The method of claim 1, further comprising administering Calcium-DTPA, Zinc-DTPA, or non-radioactive Iodine to the subject.

23. The method of claim 1, wherein the Calcium-DTPA, Zinc-DTPA, or non-radioactive Iodine is administered systemically.

24. A method for the locoregional treatment of abnormal tissue, comprising administering a composition comprising an unsealed and non-colloidal radiopharmaceutical to a subject in the region of the abnormal tissue, wherein the radiopharmaceutical comprises an effective amount of radioactivity for locoregional ablation of cells in the abnormal tissue before diffusing away from the site of administration, wherein the radiopharmaceutical is selected from the group consisting of Indium-111 chloride ($^{111}$In—Cl), Yttrium-90 chloride ($^{90}$YCl$_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP ($^{166}$Ho-DOTMP), Samarium-153 EDTMP ($^{153}$Sm-EDTMP), F-18-2-deoxy-2-fluoro-D-glucose (F-18 FDG), iododeoxyuridine, meta-iodobenzylguanidine, iodocholesterol (NP59), and combinations thereof,
  wherein the abnormal tissue comprises a neoplasm, tumor, or synovial tissue,
  wherein the administering comprises intratumoral injection, intralesional injection, intramuscular injection, intracavitary injection, interstitial injection, or intrathecal injection, and
  wherein the administering comprises administering the composition directly to the abnormal tissue.

25. A method for the locoregional treatment of tissues surrounding a post-surgical cavity, comprising administering a composition comprising an unsealed and non-colloidal radiopharmaceutical directly to tissues surrounding a post-surgical cavity in a subject, wherein the radiopharmaceutical has an effective amount of radioactivity for locoregional ablation of abnormal cells in the tissues before diffusing away from the site of introduction, wherein the radiopharmaceutical is selected from the group consisting of Indium-111 chloride ($^{111}$In—Cl), Yttrium-90 chloride ($^{90}$YCl$_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP ($^{166}$Ho-DOTMP), Samarium-153 EDTMP ($^{153}$Sm-EDTMP), F-18-2-deoxy-2-fluoro-D-glucose (F-18FDG), iododeoxyuridine, meta-iodobenzylguanidine, iodocholesterol (NP59), and combinations thereof, and
  wherein the administering comprises intratumoral injection, intralesional injection, intramuscular injection, intracavitary injection, interstitial injection, or intrathecal injection.

26. The method of claim 25, wherein the tissues surrounding the post-surgical cavity comprises unresectable micrometastases.

27. The method of claim 25, wherein the radiopharmaceutical is administered to the subject in a large injection volume that covers depths with about a 0.5 cm to 2 cm margin beyond the post-surgical cavity.

28. The method of claim 27, wherein the large injection volume covers depths with about a 1.0 cm to 1.5 cm margin beyond the post-surgical cavity.

29. The method of claim 28, wherein the radiopharmaceutical is $^{111}$In—Cl.

30. The method of claim 25, wherein the composition has a basic pH.

31. The method of claim 30, wherein the pH is from about 7.0 to about 9.0.

32. The method of claim 30, wherein the pH is up to about 14.0.

33. The method of claim 25, wherein the volume of the administered composition is at least about one tenth of one milliliter.

34. The method of claim 1, wherein the composition has a basic pH.

35. The method of claim 34, wherein the pH is from about 7.0 to about 9.0.

36. The method of claim 34, wherein the pH is up to about 14.0.

37. The method of claim 1, wherein the volume of the administered composition is at least about one tenth of one milliliter.

38. The method of claim 24, wherein the composition has a basic pH.

39. The method of claim 38, wherein the pH is from about 7.0 to about 9.0.

40. The method of claim 38, wherein the pH is up to about 14.0.

41. The method of claim 24, wherein the volume of the administered composition is at least about one tenth of one milliliter.

42. A method for the locoregional treatment of abnormal tissue, comprising administering a composition comprising an unsealed and non-colloidal radiopharmaceutical to a subject in the region of the abnormal tissue, wherein the radiopharmaceutical is locally sequestered after introduction into the abnormal tissue, and has an effective amount of radioactivity for locoregional ablation of cells in the abnormal tissue, wherein the radiopharmaceutical comprises a free radioactive metal ion selected from the group consisting of In-111, Y-90, Cu-61, Cu-62, Cu-64, Ga-66, Ga-67, Ga-68, Ho-166, Sm-153, and combinations thereof,
  wherein the abnormal tissue comprises a neoplasm, tumor, or synovial tissue,
  wherein the administering comprises intratumoral injection, intralesional injection, intramuscular injection, intracavitary injection, interstitial injection, or intrathecal injection, and
  wherein the administering comprises administering the composition directly to the abnormal tissue.

43. The method of claim 42, wherein the free radioactive metal ion comprises Y-90.

44. The method of claim 42, wherein the free radioactive metal ion comprises Ho-166.

45. The method of claim 44, wherein the radiopharmaceutical further comprises a second free radioactive metal ion.

46. The method of claim 45, wherein the second free radioactive metal ion is selected from the group consisting of In-111, Y-90, Cu-61, Cu-62, Cu-64, Ga-66, Ga-67, Ga-68, and Sm-153.

47. The method of claim 42, wherein the free radioactive metal ion comprises Sm-153.

48. The method of claim 42, wherein the free radioactive metal ion is selected from the group consisting of In-111, Cu-61, Cu-62, Cu-64, Ga-66, Ga-67, Ga-68, and combinations thereof.

49. The method of claim 42, wherein the composition has a basic pH.

50. The method of claim 49, wherein the pH is from about 7.0 to about 9.0.

51. The method of claim 49, wherein the pH is up to about 14.0.

52. The method of claim 42, wherein the volume of the administered composition is at least about one tenth of one milliliter.

53. A method for the locoregional treatment of abnormal tissue, comprising administering a composition comprising an unsealed and non-colloidal radiopharmaceutical to a subject in the region of the abnormal tissue, wherein the radiopharmaceutical is locally sequestered after introduction into the abnormal tissue, and has an effective amount of radioactivity for locoregional ablation of cells in the abnormal tissue, wherein the radiopharmaceutical is selected from the group consisting of Indium-111 chloride ($^{111}$In—Cl), Yttrium-90 chloride ($^{90}$YCl$_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate (68Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP ($^{166}$Ho-DOTMP), Samarium-153 EDTMP ($^{153}$Sm-EDTMP), F-18-2-deoxy-2-fluoro-D-glucose (F-18 FDG), iododeoxyuridine, meta-iodobenzylguanidine, iodocholesterol (NP59), and combinations thereof, wherein the composition has a basic pH,
   wherein the abnormal tissue comprises a neoplasm, tumor, or synovial tissue,
   wherein the administering comprises intratumoral injection, intralesional injection, intramuscular injection, intracavitary injection, interstitial injection, or intrathecal injection, and
   wherein the administering comprises administering the composition directly to the abnormal tissue.

54. A method for the locoregional treatment of abnormal tissue, comprising administering a composition comprising an unsealed and non-colloidal radiopharmaceutical to a subject in the region of the abnormal tissue, wherein the radiopharmaceutical comprises an effective amount of radioactivity for locoregional ablation of cells in the abnormal tissue before diffusing away from the site of administration, wherein the radiopharmaceutical is selected from the group consisting of Indium-111 chloride ($^{111}$In—Cl), Yttrium-90 chloride ($^{90}$YCl$_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP ($^{166}$Ho-DOTMP), Samarium-153 EDTMP ($^{153}$Sm-EDTMP), F-18-2-deoxy-2-fluoro-D-glucose (F-18 FDG), iododeoxyuridine, meta-iodobenzylguanidine, iodocholesterol (NP59), and combinations thereof, wherein the composition has a basic pH,
   wherein the abnormal tissue comprises a neoplasm, tumor, or synovial tissue,
   wherein the administering comprises intratumoral injection, intralesional injection, intramuscular injection, intracavitary injection, interstitial injection, or intrathecal injection, and
   wherein the administering comprises administering the composition directly to the abnormal tissue.

55. A method for the locoregional treatment of tissues surrounding a post-surgical cavity, comprising administering a composition comprising an unsealed and non-colloidal radiopharmaceutical directly to tissues surrounding a post-surgical cavity in a subject, wherein the radiopharmaceutical has an effective amount of radioactivity for locoregional ablation of abnormal cells in the tissues before diffusing away from the site of introduction, wherein the radiopharmaceutical is selected from the group consisting of Indium-111 chloride ($^{111}$In—Cl), Yttrium-90 chloride ($^{90}$YCl$_3$), Copper 61 chloride ($^{61}$Cu—Cl), Copper 62 chloride ($^{62}$Cu—Cl), Copper 64 chloride ($^{64}$Cu—Cl), Gallium 68 chloride ($^{68}$Ga—Cl), Gallium 67 chloride ($^{67}$Ga—Cl), Gallium 66 chloride ($^{66}$Ga—Cl), Gallium 68 citrate ($^{68}$Ga-citrate), Gallium 67 citrate ($^{67}$Ga-citrate), Gallium 66 citrate ($^{66}$Ga-citrate), Iodine-131 sodium iodide (Na$^{131}$I), Holmium-166 DOTMP ($^{166}$Ho-DOTMP), Samarium-153 EDTMP ($^{153}$Sm-EDTMP), F-18-2-deoxy-2-fluoro-D-glucose (F-18FDG), iododeoxyuridine, meta-iodobenzylguanidine, iodocholesterol (NP59), and combinations thereof, wherein the composition has a basic pH, and
   wherein the administering comprises intratumoral injection, intralesional injection, intramuscular injection, intracavitary injection, interstitial injection, or intrathecal injection.

* * * * *